United States Patent
Merchant

(10) Patent No.: US 11,680,090 B2
(45) Date of Patent: Jun. 20, 2023

(54) INTERLEUKIN-2 FUSION PROTEINS AND USES THEREOF

(71) Applicant: Medicenna Therapeutics Inc., Toronto (CA)

(72) Inventor: Fahar Merchant, Vancouver (CA)

(73) Assignee: Medicenna Therapeutics, Inc., Toronto (CA)

( * ) Notice: Subject to any disclaimer, the term of this patent is extended or adjusted under 35 U.S.C. 154(b) by 186 days.

(21) Appl. No.: 16/992,068

(22) Filed: Aug. 12, 2020

(65) Prior Publication Data

US 2021/0246183 A1    Aug. 12, 2021

Related U.S. Application Data

(62) Division of application No. 15/024,792, filed as application No. PCT/CA2014/050917 on Sep. 24, 2014, now Pat. No. 10,781,242.

(60) Provisional application No. 61/881,931, filed on Sep. 24, 2013.

(51) Int. Cl.
| | | |
|---|---|---|
| A61K 38/17 | (2006.01) | |
| A61K 38/20 | (2006.01) | |
| C07K 14/47 | (2006.01) | |
| C07K 14/55 | (2006.01) | |
| C07K 14/82 | (2006.01) | |
| C12N 5/071 | (2010.01) | |
| C12N 15/63 | (2006.01) | |
| C07K 19/00 | (2006.01) | |
| A61K 38/00 | (2006.01) | |

(52) U.S. Cl.
CPC .......... *C07K 14/55* (2013.01); *A61K 38/1761* (2013.01); *A61K 38/2013* (2013.01); *C07K 14/4747* (2013.01); *C07K 14/82* (2013.01); *C07K 19/00* (2013.01); *C12N 5/0602* (2013.01); *C12N 15/63* (2013.01); *A61K 38/00* (2013.01); *C07K 2319/00* (2013.01); *C07K 2319/33* (2013.01)

(58) Field of Classification Search
CPC ................ A61K 38/2013; A61K 38/17; A61K 38/1761; A61K 38/20; C07K 14/55; C07K 14/54; C07K 14/47; C07K 14/4747
See application file for complete search history.

(56) References Cited

U.S. PATENT DOCUMENTS

| | | | |
|---|---|---|---|
| 4,522,811 A | 6/1985 | Eppstein et al. | |
| 4,530,787 A | 7/1985 | Shaked et al. | |
| 4,569,790 A | 2/1986 | Koths et al. | |
| 4,572,798 A | 2/1986 | Koths et al. | |
| 4,604,377 A | 8/1986 | Fernandes et al. | |
| 4,656,132 A | 4/1987 | Ben-Bassat et al. | |
| 4,738,927 A | 4/1988 | Taniguchi et al. | |
| 4,748,234 A | 5/1988 | Dorin et al. | |
| 4,816,249 A | 5/1989 | Levy et al. | |
| 4,931,543 A | 6/1990 | Halenbeck et al. | |
| 5,068,177 A | 11/1991 | Carson et al. | |
| 5,122,464 A | 6/1992 | Wilson et al. | |
| 5,227,159 A | 7/1993 | Miller | |
| 5,538,866 A | 7/1996 | Israeli et al. | |
| 6,011,002 A | 1/2000 | Pastan et al. | |
| 6,451,308 B1 | 9/2002 | Strom et al. | |
| 6,468,798 B1 | 10/2002 | Debs et al. | |
| 6,617,135 B1 | 9/2003 | Gillies et al. | |
| 6,682,736 B1 | 1/2004 | Hanson et al. | |
| 6,984,720 B1 | 1/2006 | Korman et al. | |
| 7,001,596 B1 | 2/2006 | Johnson et al. | |
| 7,288,638 B2 | 10/2007 | Jure-Kunkel et al. | |
| 7,569,215 B2 | 8/2009 | Wittrup | |
| 7,741,465 B1 | 6/2010 | Eshhar et al. | |
| 7,812,135 B2 | 10/2010 | Smith et al. | |
| 7,943,743 B2 | 5/2011 | Korman et al. | |
| 8,008,449 B2 | 8/2011 | Korman et al. | |
| 8,217,149 B2 | 7/2012 | Irving et al. | |
| 8,337,850 B2 | 12/2012 | Ahrens et al. | |
| 8,355,502 B1 | 1/2013 | Donlin et al. | |
| 8,821,867 B2 | 9/2014 | Ahrens et al. | |
| 8,962,804 B2 | 2/2015 | Williams et al. | |
| 9,428,567 B2 | 8/2016 | Garcia | |
| 9,468,678 B2 | 10/2016 | Ahrens et al. | |
| 10,781,242 B2 * | 9/2020 | Merchant .......... | C07K 14/4747 |
| 2002/0039581 A1 | 4/2002 | Carreno et al. | |
| 2002/0086014 A1 | 7/2002 | Korman et al. | |
| 2003/0138405 A1 | 7/2003 | Fueyo et al. | |
| 2005/0201994 A1 | 9/2005 | Korman et al. | |

(Continued)

FOREIGN PATENT DOCUMENTS

| | | |
|---|---|---|
| EP | 338841 | 10/1989 |
| WO | WO 1991/002000 | 2/1991 |

(Continued)

OTHER PUBLICATIONS

Hodge et al. Surface and intracellular interleukin-2 receptor expression on various resting and activated populations involved in cell-mediated immunity in human peripheral blood. Scand J Immunol 51: 67-72, 2000.*

Mitra et al. Biology of IL-2 and its therapeutic modulation: mechanisms and strategies. J Leukoc Biol 103: 643-655, 2018.*

Adams PD, et al. Identification of a cyclin-cdk2 recognition motif present in substrates and p21-like cyclin-dependent kinase inhibitors. Mol Cell Biol. 16(12), 6623-6633 (1996).

(Continued)

*Primary Examiner* — Bridget E Bunner
(74) *Attorney, Agent, or Firm* — Morgan, Lewis & Bockius LLP

(57) ABSTRACT

The present invention relates to interleukin-2 fusion proteins. More specifically, the invention provides, in part, fusion proteins that include a interleukin-2 protein moiety joined to a Bcl-2 family member protein moiety.

17 Claims, 2 Drawing Sheets

Specification includes a Sequence Listing.

(56) References Cited

U.S. PATENT DOCUMENTS

| | | | |
|---|---|---|---|
| 2006/0147420 | A1 | 7/2006 | Fueyo et al. |
| 2006/0160187 | A1 | 7/2006 | Denis-Mize |
| 2006/0269515 | A1 | 11/2006 | Denis-Mize |
| 2010/0183545 | A1 | 7/2010 | Puri |
| 2010/0240732 | A1 | 9/2010 | Gilboa |
| 2010/0317577 | A1* | 12/2010 | Youle ............... C07K 14/4747 |
| | | | 435/375 |
| 2011/0150892 | A1 | 6/2011 | Thudium et al. |
| 2011/0017219 | A1 | 7/2011 | Merchant |
| 2011/0274650 | A1 | 11/2011 | Garin et al. |
| 2011/0274685 | A1 | 11/2011 | Keler et al. |
| 2012/0213771 | A1 | 8/2012 | Keler et al. |
| 2012/0315245 | A1 | 12/2012 | Leon Monzon et al. |
| 2013/0022623 | A1 | 1/2013 | Karsunky et al. |
| 2013/0149236 | A1 | 6/2013 | Johnson et al. |
| 2014/0046026 | A1 | 2/2014 | Garcia |
| 2015/0203848 | A1 | 7/2015 | Yu |
| 2015/0268243 | A1 | 9/2015 | Hannani |
| 2016/0222117 | A1 | 8/2016 | Irving et al. |
| 2016/0237135 | A1* | 8/2016 | Merchant ............... C12N 15/63 |
| 2016/0257758 | A1 | 9/2016 | Gray et al. |
| 2017/0081409 | A1 | 3/2017 | Dijk et al. |
| 2017/0281764 | A1 | 10/2017 | Tso et al. |

FOREIGN PATENT DOCUMENTS

| | | |
|---|---|---|
| WO | WO 1999/045128 | 9/1999 |
| WO | WO 1999/060128 | 11/1999 |
| WO | WO 2001/027156 | 4/2001 |
| WO | WO 2001/036650 | 5/2001 |
| WO | WO 2003/048334 | 6/2003 |
| WO | WO 2005/007121 | 1/2005 |
| WO | WO 2006/029879 | 3/2006 |
| WO | WO 2006/081510 | 8/2006 |
| WO | WO 2008/039173 | 4/2008 |
| WO | WO 2010/077634 | 7/2010 |
| WO | WO 2010/096418 | 8/2010 |
| WO | WO 2012/032433 | 3/2012 |
| WO | WO 2012/054929 | 4/2012 |
| WO | WO 2012/088446 | 6/2012 |
| WO | WO 2010/085495 | 7/2012 |
| WO | WO 2012/119093 | 9/2012 |
| WO | WO 2012/120125 | 9/2012 |
| WO | WO 2013/006490 | 1/2013 |
| WO | WO 2013/038066 | 3/2013 |
| WO | WO 2013/079174 | 6/2013 |
| WO | WO 2014/127261 | 8/2014 |
| WO | WO 2015/009856 | 1/2015 |
| WO | WO 2015/042707 | 4/2015 |
| WO | WO 2015/117229 | 8/2015 |
| WO | WO 2015/164815 | 10/2015 |
| WO | WO 2016/145085 | 9/2016 |
| WO | WO 2017/100541 | 6/2017 |

OTHER PUBLICATIONS

Adams PD, et al. Transcriptional control by E2F. Semin. Cancer Biol. 6(2), 99-108 (1995).

Allen C, et al. Interleukin-13 Displaying Retargeted Oncolytic Measles Virus Strains Have Significant Activity Against Gliomas With Improved Specificity. Mol Ther. 16(9), 1556-1564 (2008).

Antignani et al., "A Chimeric Protein Induces Tumor Cell Apoptosis by Delivering the Human Bcl-2 Family BH3-Only Protein Bad", Biochemistry, vol. 44, 2005, p. 4074-4082.

Antignani et al., "The cytokine, Granulocyte-Macrophage Colony-Stimulating Factor (GM-CSF), Can Deliver Bxl-XL as an Extracellular Fusion Protein to Protect Cells from Apoptosis and Retain Differentiation Induction", The Journal of Biological Chemistry, vol. 282, No. 15, 2007, p. 11246-11254.

Aqeilan et al., "Interleukin 2-Bax: a novel prototype of human chimeric proteins for targeted therapy", FEBS Letters, vol. 457, 1999, pp. 271-276.

Aqeilan et al., "Mechanism of action of interleukin-2 (IL-2)-Bax, an apoptosis-inducing chimaeric protein targeted against cells expressing the IL-2 receptor", Biochemical Journal, vol. 370, 2003, pp. 129-140.

Argos "A possible homology between immunodeficiency virus p24 core protein and picornaviral VP2 coat protein: prediction of HIV p24 antigenic sites" EMBO Journal, vol. 8, No. 3, pp. 779-785 (1989).

Azar et al., "GnRH-Bik/Bax/Bak chimeric proteins target and kill adenocarcinoma cells; the general use of pro-apoptotic proteins of the Bcl-2 family as novel killing components of targeting chimeric proteins", Apoptosis, vol. 5, 2000, p. 531-542.

Baldari C, et al. A novel leader peptide which allows efficient secretion of a fragment of human interleukin 1 beta in *Saccharomyces cerevisiae*. EMBO J. 6(1), 229-234 (1987).

Batlevi CL, et al. Novel immunotherapies in lymphoid malignancies. Nat Rev Clin Oncol. 13(1), 25-40 (2016).

Beers & Berkow, The Merck Manual, 17$^{th}$ edition, pp. 986-995, (1999).

Berk AJ. Adenovirus Promoters and E1a Transactivation. Annual Review of Genetics. 20(1), 45-77 (1986).

Bhatia et al. Innovative approaches for enhancing cancer gene therapy. Discovery Med 15(84): 309-317, 2013.

Blanar MA, et al. Interaction cloning: identification of a helix-loop-helix zipper protein that interacts with c-Fos. Science. 256(5059), 1014-1018 (1992).

Blaser et al. "Donor-derived IL-15 is critical for acute allogeneic graft-versus-host disease" Blood, vol. 105, pp. 894-901 (2005).

Boder ET, et al. Yeast surface display for screening combinatorial polypeptide libraries. Nat. Biotechnol. 15(6), 553-557 (1997).

Bolt, et al. The generation of a humanized, non-mutagenic CD3 monoclonal antibody which retains in vitro immunosuppressive properties. Eur J Immunol 23: 403-411, 1993.

Bork, P. Powers and pitfalls in sequence analysis: the 70% hurdle. Genome Res 10: 398-400, 2000.

Bork, et al. Go hunting in sequence databases but watch out for the traps. Trends in Genetics. 12(10): 425-427, 1996.

Borrok, et al. An "Fc-silenced" igG1 format with extended half-life designed for improved stability. J Phamaceut Sci 106: 1008-1017, Jan. 2017.

Boyman et al. "The role of interleukin-2 during homeostasis and activation of the immune system" Nature Reviews Immunology, vol. 12, pp. 180-190 (2012).

Brenner, S.E. Errors in genome annotation. Trends in Genetics 15(4): 132-133, 1999.

Buchli et al., "The Functional Display of Interleukin-2 on Filamentous Phage" Archives of Biochemistry and Biophysics, vol. 339, pp. 79-84 (1997).

Cao et al. In vivo delivery of a Bcl-xL fusion protein containing the TAT protein transduction domain protects against ischemic brani injury and neuronal apoptosis. J Neurosci 22(13): 5423-5431, 2002.

Carmenate et al., Human IL-2 mutein with higher antitumor efficacy than wild type IL-2. J Immunol 190: 6230-6238, 2013.

Cassell et al., Current Pharmaceutical Design, vol. 8, No. 24, Nov. 2002, pp. 2171-2183(13).

Cate RL, et al. Isolation of the bovine and human genes for Müllerian inhibiting substance and expression of the human gene in animal cells. Cell. 45(5), 685-698 (1986).

Ceretti et al., "Cloning, sequence, and expression of bovine interleukin 2", Proc. Natl. Acad. Sci. U.S.A. 83 (10), pp. 3223-3227. (1986) & CA Registry Nos. 103207-23-4 & 103219-24-5.

Cheng G, et al. T cell tolerance and the multi-functional role of IL-2R signaling in T regulatory cells. Immunol Rev. 241(1), 63-76 (2011).

Clinical Trial NCT02964078 history, dated Nov. 15, 2016 (10 total pages).

Clinical Trial NCT02989714 history, dated Dec. 12, 2016 (8 total pages).

Doerks et al. Protein annotation: detective work for function prediction. Trends in Genetics 14(6): 248-250, 1998.

Dumont "Interleukin-2 Family Cytokines: Potential for Therapeutic Immunoregulation" Expert Opinion Therapeutic Patents, vol. 15, No. 5, pp. 521-554 (2005).

(56) References Cited

OTHER PUBLICATIONS

European Search Report dated Oct. 17, 2017, for EP Application No. 15782644.7, 8 pages.
Freyer GA, et al. Characterization of the major mRNAs from adenovirus 2 early region 4 by cDNA cloning and sequencing. Nucleic Acids Res. 12(8), 3503-3519 (1984).
Fujita T, et al. Structure of the human interleukin 2 gene. Proceedings of the National Academy of Sciences. 80(24), 7437-7441 (1983).
GenBank Accession No. AAN76508, IL-2 (Bos taurus), Submission date Feb. 13, 2001.
GenBank Accession No. AAP83420, Interleukin-2 (Bos grunniens), Submission date May 7, 2003.
GenBank Accession No. AAW27917, Interleukin-2 (Moschus berezovskii), Submission date Nov. 26, 2004.
Genbank Accession No. NM_000206, *Homo sapiens* interleukin receptor subunit gamma [*Homo sapiens*] Jun. 24, 2018.
Genbank Accession No. NM_000878, *Homo sapiens* interleukin 2 receptor subunit beta (IL2RB) [*Homo sapiens*] Jun. 30, 2018.
Genbank Accession No. NM_013563, Mus musculus interleukin 2 receptor, gamma chain (IL2rg) [house mouse] Jul. 7, 2018.
Genbank Accession No. NP_000197, cytokine receptor common subunit gamma precursor [*Homo sapiens*] Jun. 24, 2018.
Genbank Accession No. NP_000869, interleukin-2 receptor subunit beta precursor [*Homo sapiens*] Jun. 30, 2018.
Genbank Accession No. NP_038591, cytokine receptor common subunit gamma isoform a precursor [house mouse] Jul. 7, 2018.
Gilardi P, et al. The E4 transcriptional unit of Ad2: far upstream sequences are required for its transactivation by E1A. Nucleic Acids Res. 12(20), 7877-7888 (1984).
Gilardi P, et al. The E4 promoter of adenovirus type 2 contains an E1A dependent cis-acting element. Nucleic Acids Res. 14(22), 9035-9049 (1986).
Grant, et al., "The interleukin 2 receptor (IL-2R): The IL-2R α subunit alters the function of the IL-2R β subunit to enhance IL-2 binding and signaling by mechaisms that do not require binding of IL-2 to IL-2R α subunit," Proc. Natl. Acad. Sci. USA, vol. 89, pp. 2165-2169 (1992).
Hamanishi et al. PD-1/PD-L1 blockade in cancer treatment: perspectives and issues. Int J Clin Oncol 21: 462-473, 2016.
Hanaka S, et al. Regulation of in vitro and in vivo transcription of early-region IV of adenovirus type 5 by multiple cis-acting elements. Mol Cell Biol. 7(7), 2578-2587 (1987).
Hannani, et al. Anticancer therapy by CTLA-4 blockade: obligatory contribution of IL-2 receptor and negative prognostic impact of soluble CD25. Cell Res 25: 208-224, 2015.
Hatfield L, et al. The NFIII/OCT-1 binding site stimulates adenovirus DNA replication in vivo and is functionally redundant with adjacent sequences. J Virol. 67(7), 3931-3939 (1993).
Huang et al. IL-2 synergizes with PD-1/PD-L1 blockade via CD28/CHK1 pathway to enhance CD81 T cell responses in lung squamous cell carcinoma. Annals Oncol 27 (Suppl 9): ix123-ix125, abstract 653, 2016.
Johnson DG, et al. Autoregulatory control of E2F1 expression in response to positive and negative regulators of cell cycle progression. Genes Dev. 8(13), 1514-1525 (1994).
Jones C, et al. E1A-mediated activation of the adenovirus E4 promoter can occur independently of the cellular transcription factor E4F. Mol Cell Biol. 11(9), 4297-4305 (1991).
Ju et al. "CP-690,550, a therapeutic agent, inhibits cytokine-mediated Jak3 activation and proliferation of T cells from patients withATL and HAM/TSP" Blood, vol. 117, No. 6, pp. 1938-1946 (2011).
Juengst, E.T. What next for gene therapy? BMJ 326: 1410-1411, 2003.
Kahlon KS, et al. Specific Recognition and Killing of Glioblastoma Multiforme by Interleukin 13-Zetakine Redirected Cytolytic T Cells. Cancer Res. 64(24), 9160-9166 (2004).
Kaufman HL, et al. Oncolytic viruses: a new class of immunotherapy drugs. Nat Rev Drug Discov. 14(9), 642-662 (2015).
Kaufman RJ, et al. Construction of a modular dihydrofolate reductase cDNAgene: analysis of signals utilized for efficient expression. Mol Cell Biol. 2(11), 1304-1319 (1982).
Kaufman RJ, et al. Translational efficiency of polycistronic mRNAs and their utilization to express heterologous genes in mammalian cells. The EMBO Journal. 6(1), 187-193 (1987).
Kong S, et al. Suppression of Human Glioma Xenografts with Second-Generation IL13R-Specific Chimeric Antigen Receptor-Modified T Cells. Clin Cancer Res. 18(21), 5949-5960 (2012).
Kurjan J, et al. Structure of a yeast pheromone gene (MF alpha): a putative alpha-factor precursor contains four tandem copies of mature alpha-factor. Cell. 30(3), 933-943 (1982).
Kuziel et al. Unexpected effects of the IL-2 receptor alpha subunit on high affinity IL-2 receptor assembly and function detected with a mutant IL-2 analog. J Immunol 150; 3357-3365, 1993.
Leclair KP, et al. The p50 subunit of NF-kappa B associates with the NF-IL6 transcription factor. Proc Natl Acad Sci U S A. 89(17), 8145-8149 (1992).
Lee KA, et al. A cellular transcription factor E4F1 interacts with an E1a-inducible enhancer and mediates constitutive enhancer function in vitro. The EMBO Journal. 6(5), 1345-1353 (1987).
Lee SJ, et al. Proliferin secreted by cultured cells binds to mannose 6-phosphate receptors. J. Biol. Chem. 263(7), 3521-3527 (1988).
Lenardo MJ. Interleukin-2 programs mouse alpha beta T lymphocytes for apoptosis. Nature. 353(6347), 858-861 (1991).
Levin AM, et al. Exploiting a natural conformational switch to engineer an Interleukin-2 superkine. Nature. 484(7395), 529-533 (2012).
Liao W, et al. Interleukin-2 at the Crossroads of Effector Responses, Tolerance, and Immunotherapy. Immunity. 38(1), 13-25 (2013).
Liao W, et al. Cytokine receptor modulation by interleukin-2 broadly regulates T helper cell lineage differentiation. Nat Immunol. 12(6), 551-559 (2011).
Liao W, et al. Priming for T helper type 2 differentiation by interleukin 2-mediated induction of IL-4 receptor α chain expression. Nat Immunol. 9(11), 1288-1296 (2008).
Liu et al. Ongoing clinical trials of PD-1 and PD-L1 inhibitors for lung cancer in China. J Hematol Oncol 10: 136, 2017 (8 total pages).
Luckow VA, et al. High level expression of nonfused foreign genes with Autographa californica nuclear polyhedrosis virus expression vectors. Virology. 170(1), 31-39 (1989).
Lyu et al., "Bax345/BLyS: A novel, completely human fusion protein targeting malignant B cells and delivering a unique mitochondrial toxin", Cancer Letters, vol. 322, 2012, p. 159-168.
Mccaffrey AP, et al. RNA interference in adult mice. Nature. 418(6893), 38-39 (2002).
Mitra et al. "Interleukin-2 Activity Can Be Fine Tuned With Engineered Receptor Signaling Clamps", Cell Press, vol. 42, pp. 826-838, 2015.
Morgan DA, et al. Selective in vitro growth of T lymphocytes from normal human bone marrows. Science. 193(4257), 1007-1008 (1976).
Morris et al. "Preclinical and phase I clinical trial of blockade of IL-15 using Mik 1 monoclonal antibody in T cell large granular lymphocyte leukemia" PNAS, vol. 103, No. 2, pp. 401-406 (2006).
Murray, E.J. "Cloning Genes in Mammalian Cell-lines" in Molecular Biology and Biotechnology. Great Britain: The Royal Society of Chemistry, 2000, pp. 177-201.
Neuman E, et al. Transcription of the E2F-1 gene is rendered cell cycle dependent by E2F DNA-binding sites within its promoter. Mol Cell Biol. 15(8), 4660 (1995).
Neuman E, et al. Structure and partial genomic sequence of the human E2F1 gene. Gene. 173(2), 163-169 (1996).
Ngo et al. Computational complexity, protein structure prediction, and the Levinthal paradox. The Protein Folding Problem and Tertiary Structure Prediction, pp. 492-495, 1994.
Ohaegbulam et al. Human cancer immunotherapy with antibodies to the PD-1 and PD-L1 pathway. Trends Mol Med 21(1): 24-33, 2015.
Ott et al. CTLA-4 and PD-1/PD-L1 blockade: new immunotherapeutic modalities with durable clinical benefit in melanoma patients. Clin Cancer Rest 19(19): 5300-5309, 2013.
Parr MJ, et al. Tumor-selective transgene expression in vivo mediated by an E2F-responsive adenoviral vector. Nat. Med. 3(10), 1145-1149 (1997).

(56) References Cited

OTHER PUBLICATIONS

Phillips. A. J. The challenge of gene therapy and DNA delivery. J Pharmacy Pharmacol 53: 1169-1174, 2001.
Putnam DA. Antisense strategies and therapeutic applications. Am J Health Syst Pharm. 53(2), 151-160; quiz 182-183 (1996).
Rao et al. Interleukin-2 mutants with enhanced alpha-receptor subunit binding affinity. Protein Engineering 16(12): 1081-1087, 2003.
Rawlins DR, et al. Structure and function of the adenovirus origin of replication. Cell. 37(1), 309-319 (1984).
Rosenberg SA, et al. Biological activity of recombinant human interleukin-2 produced in *Escherichia coli*. Science. 223(4643), 1412-1414 (1984).
Rosenfeld PJ, et al. Sequence-specific interactions between cellular DNA-binding proteins and the adenovirus origin of DNA replication. Mol. Cell. Biol. 7(2), 875-886 (1987).
RUBANYI e, G.M. The future of human gene therapy. Mol Aspects Med 22: 113-142, 2001.
Schmid S.I., et al. Selective encapsidation of adenovirus DNA. Current Topics in Microbiology and Immunology, 199(1), 67-80 (1995).
Schultz LD, et al. Expression and secretion in yeast of a 400-kDa envelope glycoprotein derived from Epstein-Barr virus. Gene. 54(1), 113-123 (1987).
Seed B. An LFA-3 cDNA encodes a phospholipid-linked membrane protein homologous to its receptor CD2. Nature. 329(6142), 840-842 (1987).
Segel et al., "Effect of IL-2-Bax, a novel interleukin-2-receptor-targeted chimeric protein, on bleomycin lung injury". Int'l Journal of Experimental Pathology, vol. 86, 2005, p. 279-288.
Sellers WR, et al. A potent transrepression domain in the retinoblastoma protein induces a cell cycle arrest when bound to E2F sites. Proc Natl Acad Sci U S A. 92(25), 11544-11548 (1995).
Shanafelt et al., "A T-cell-selective interleukin 2 mutein exhibits potent antitumor activity and is well tolerated in vivo," Nature Biotechnology, vol. 18, pp. 1197-1202 (2000).
Shevach "Application of IL-2 therapy to target T regulatory cell function" Trends in Immunology, vol. 33, No. 12, pp. 626-632 (2012).
Skolnick et al. From genes to protein structure and function: novel applications of computational approaches in the genomic era. Trends in Biotech 18(1): 34-39, 2000.
Smith et al. The challenges of genome sequence annotation or "The devil is in the details". Nature Biotech 15: 1222-1223, 1997.
Smith GE, et al. Modification and secretion of human interleukin 2 produced in insect cells by a baculovirus expression vector. Proc Natl Acad Sci U S A. 82(24), 8404-8408 (1985).
Smith GE, et al. Production of human beta interferon in insect cells infected with a baculovirus expression vector. Mol Cell Biol. 3(12), 2156-2165 (1983).
Spangler et al. Insights into cytokine-receptor interactions from cytokine engineering. Annu Rev Immunol 33: 139-167, 2015.

Strohl "Optimization of Fc-mediated effector functions of monoclonal antibodies" vol. 20, issue 6, pp. 685-691 (2009).
Tanaka et al. Structure-function analysis of the Bcl-2 oncoprotein. J Biol Chem 268(15): 10920-10926, 1993.
Taniguchi T, et al. Structure and expression of a cloned cDNA for human interleukin-2. Nature. 302(5906), 305-310 (1983).
Thaci B, et al. Significance of interleukin-13 receptor alpha 2-targeted glioblastoma therapy. Neuro Oncol. 16(10), 1304-1312 (2014).
Tigges MA, et al. Splice junctions in adenovirus 2 early region 4 mRNAs: multiple splice sites produce 18 to 24 RNAs. J Virol. 50(1), 106-117 (1984).
Tokuriki et al. Stability effects of mutations and protein evolvability. Curr Opin Structural Biol 19: 596-604, 2009.
Tsudo et al., "Characterization of the interleukin 2 receptor β chain using three distinct monoclonal antibodies," Proc. Natl. Acad. Sci. USA, vol. 86, pp. 1982-1986 (1989).
Twumasi-Boateng K, et al. Oncolytic viruses as engineering platforms for combination immunotherapy. Nat. Rev. Cancer. 18(7), 419-432 (2018).
UNIPROTKB/Swiss Prot Accession Q07817, Feb. 1, 1995, 14 total pages.
Vallera et al., "Retroviral Immunotoxin Gene Therapy of Leukemia in Mice Using Leukemia-Specific T Cells Transduced with an Interleukin-3/Bax Fusion Protein Gene", Human Gene Therapy, vol. 14, 2003, p. 1787-1798.
Virdee et al., "Phosphorylation of the pro-apoptotic protein BAD on serine 155, a novel site, contributes to cell survival", Current Biology, vol. 10, No. 18, 2000, pp. 1151-1154.
Virtanen A, et al. mRNAs from human adenovirus 2 early region 4. J Virol. 51(3), 822-831 (1984).
Vogelstein B, et al. Cancer Genome Landscapes. Science. 339(6127), 1546-1558 (2013).
Votavova et al. "Increasing the biological activity of IL-2 and IL-15 through complexing with anti-IL-2 mAbs and IL-15R[alpha]-Fc chimera" Immunology Letters, vol. 159, No. 1-2, pp. 1-10 (2014).
Wells, J.A. Additivity of mutational effects in proteins. Biochemistry 29 (37): 8509-8517, 1990.
West, et al. PD-L1 blockade synergizes with IL-2 therapy in reinvigorating exhausted T cells. J Clin Invest 123(6): 2604-2615, 2013.
Wides RJ, et al. Adenovirus origin of DNA replication: sequence requirements for replication in vitro. Mol. Cell. Biol. 7(2), 864-874 (1987).
Xia H, et al. siRNA-mediated gene silencing in vitro and in vivo. Nat. Biotechnol. 20(10), 1006-1010 (2002).
Yan et al. Overexpression of the cell death suppressor Bcl-w in ischemic brain: implications for a neuroprotective role via the mitochondrial pathway. J Cerebral Blood Flow Metabol 20: 620-630, 2000.
Zhu J, et al. Differentiation of Effector CD4 T Cell Populations. Annu Rev Immunol. 28, 445-489 (2010).
Zurawski et al. Partial agonist/antagonist mouse interleukin-2 proteins indicate that a third component of the receptor complex functions in signal transduction. EMBO J 9(12): 3899-3905, 1990.

\* cited by examiner

Fig. 2A. 927 bp proS2-Bad cDNA cloned into *BamHI* and *XhoI* sites of pGW07 expression vector.

ATGCCGACCTCTAGCTCTACCAAAAAGACGCAATTGCAACTGGAGCACCTTTTGCTGGATCTGCAGATGATTCTGA
ATGGTATCAACAACTACAAGAACCCGAAACTGACCCGTATGCTGACGGCCAAATTCTACATGCCTAAGAAAGCGA
CCGAGCTGAAGCACTTGCAATGCCTGGAAGAAGAACTGAAGCCGCTGGAAGAAGTCCTGAATCTGGCGCAGTCC
AAAAACTTCCACTTTGACCCACGTGATGTGGTTAGCAACATCAATGTCTTTGTCCTGGAGCTCAAAGGTAGCGAGA
CTACCTTCATGTGTGAGTACGCGGACGAAACTGCGACCATTGTGGAGTTCCTGAACCGTTGGATCACGTTCAGCCA
GTCCATCATTAGCACGCTGACCGGTAGCTTTCAGATCCCGGAATTTGAGCCGAGCGAGCAAGAGGATTCAAGCAG
CGCGGAGCGCGGTCTGGGTCCGAGCCCGGCAGGCGACGGTCCGAGCGGCAGCGGCAAGCATCACCGCCAGGCG
CCAGGCCTGCTGTGGGATGCATCGCATCAACAGGAACAACCGACGAGCAGCAGCCATCATGGTGGCGCTGGTGC
GGTTGAGATTAGATCGCGCCACTCCGCATATCCTGCCGGCACCGAAGATGACGAAGGCATGGGCGAGGAACCGA
GCCCGTTCCGTGGCCGTAGCCGTGCTGCACCGCCGAATCTGTGGGCCGCACAGCGTTATGGTCGCGAGTTGCGTC
GCATGTCCGACGAGTTTGTTGACTCCTTCAAGAAAGGTTTACCGCGTCCGAAATCTGCCGGTACCGCGACGCAGAT
GCGTCAGAGCAGCAGCTGGACCCGCGTGTTTCAATCTTGGTGGGATCGTAATCTGGGTCGTGGTAGCAGCGCACC
GAGCCAACACCACCATCACCATCACTAA (SEQ ID NO: 16 with a poly-histidine tag).

Fig. 2B. proS2-BAD protein translation. MW 34.6 kDa, pI 6.9. BAD domain is bolded.

MPTSSSTKKTQLQLEHLLLDLQMILNGINNYKNPKLTRMLTAKFYMPKKATELKHLQCLEEELKPLEEVLNLAQSKNFHF
DPRDVVSNINVFVLELKGSETTFMCEYADETATIVEFLNRWITFSQSIISTLTGS**FQIPEFEPSEQEDSSSAERGLGPSPAG
DGPSGSGKHHRQAPGLLWDASHQQEQPTSSSHHGGAGAVEIRSRHSAYPAGTEDDEGMGEEPSPFRGRSRAAPP
NLWAAQRYGRELRRMSDEFVDSFKKGLPRPKSAGTATQMRQSSS**WTRVFQSWWDRNLGRGSSAPSQHHHHHH
(SEQ ID NO: 17 with a poly-histidine tag).

SEQUENCE LISTING

```
<160> NUMBER OF SEQ ID NOS: 20

<210> SEQ ID NO 1
<211> LENGTH: 132
<212> TYPE: PRT
<213> ORGANISM: Homo sapiens

<400> SEQUENCE: 1

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
```

```
                    20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ala Gln Ser Ile Ile
        115                 120                 125

Ser Thr Leu Thr
        130

<210> SEQ ID NO 2
<211> LENGTH: 132
<212> TYPE: PRT
<213> ORGANISM: Artificial Sequence
<220> FEATURE:
<223> OTHER INFORMATION: synthetic IL-2 variant

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala His Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 3
<211> LENGTH: 132
<212> TYPE: PRT
<213> ORGANISM: Artificial Sequence
<220> FEATURE:
<223> OTHER INFORMATION: synthetic IL-2 variant ProS2

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Ala Lys Phe Tyr Met Pro Lys Lys
            35                  40                  45
```

Ala Thr Glu Leu Lys His Leu Gln Cys Leu Glu Glu Leu Lys Pro
    50                  55                  60

Leu Glu Glu Val Leu Asn Leu Ala His Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 4
<211> LENGTH: 136
<212> TYPE: PRT
<213> ORGANISM: Artificial Sequence
<220> FEATURE:
<223> OTHER INFORMATION: synthetic IL-2 variant cpProS2

<400> SEQUENCE: 4

Met Leu Thr Ala Lys Phe Tyr Met Pro Lys Lys Ala Thr Glu Leu Lys
1               5                   10                  15

His Leu Gln Cys Leu Glu Glu Glu Leu Lys Pro Leu Glu Glu Val Leu
            20                  25                  30

Asn Leu Ala His Ser Lys Asn Phe His Phe Asp Pro Arg Asp Val Val
        35                  40                  45

Ser Asn Ile Asn Val Phe Val Leu Glu Leu Lys Gly Ser Glu Thr Thr
    50                  55                  60

Phe Met Cys Glu Tyr Ala Asp Glu Thr Ala Thr Ile Val Glu Phe Leu
65                  70                  75                  80

Asn Arg Trp Ile Thr Phe Ser Gln Ser Ile Ile Ser Thr Leu Thr Gly
                85                  90                  95

Gly Asn Gly Gly Pro Thr Ser Ser Ser Thr Lys Lys Thr Gln Leu Gln
            100                 105                 110

Leu Glu His Leu Leu Leu Asp Leu Gln Met Ile Leu Asn Gly Ile Asn
        115                 120                 125

Asn Tyr Lys Asn Pro Lys Leu Thr
    130                 135

<210> SEQ ID NO 5
<211> LENGTH: 399
<212> TYPE: DNA
<213> ORGANISM: Artificial Sequence
<220> FEATURE:
<223> OTHER INFORMATION: synthetic IL-2 variant proS2

<400> SEQUENCE: 5
atgccgacct ctagctctac caaaaagacg caattgcaac tggagcacct tttgctggat      60
ctgcagatga ttctgaatgg tatcaacaac tacaagaacc cgaaactgac ccgtatgctg     120
acggccaaat tctacatgcc taagaaagcg accgagctga agcacttgca atgcctggaa     180
gaagaactga agccgctgga agaagtcctg aatctggcgc agtccaaaaa cttccacttt     240
gacccacgtg atgtggttag caacatcaat gtctttgtcc tggagctcaa aggtagcgag     300
actaccttca gtgtgagta cgcggacgaa actgcgacca ttgtggagtt cctgaaccgt     360
tggatcacgt tcagccagtc catcattagc acgctgacc                            399

<210> SEQ ID NO 6
<211> LENGTH: 408
<212> TYPE: DNA
<213> ORGANISM: Artificial Sequence
<220> FEATURE:
<223> OTHER INFORMATION: synthetic IL-2 variant cpProS2

<400> SEQUENCE: 6

```
atgctgaccg cgaaattcta catgccaaag aaagcgaccg agctgaaaca cttgcaatgc      60
ctggaagaag agttgaagcc gctggaagaa gtcctgaatc tggcccagtc caagaacttt     120
cacttcgatc gcgtgacgt tgtctctaac atcaatgtgt tgtcctgga gctgaagggt       180
agcgaaacca cgttcatgtg tgagtacgcg acgaaactg cgacgattgt ggagttcctg      240
aatcgttgga ttacgttctc tcagtccatt atcagcacgc tgaccggtgg taatggtggc    300
cctaccagca gcagcaccaa gaaaactcag ctgcaactgg agcacttgct gctggatctg    360
caaatgatcc tcaacggtat caacaactac aaaaacccga aacttacc                  408
```

<210> SEQ ID NO 7
<211> LENGTH: 232
<212> TYPE: PRT
<213> ORGANISM: Homo sapiens

<400> SEQUENCE: 7

```
Ser Gln Ser Asn Arg Glu Leu Val Val Asp Phe Leu Ser Tyr Lys Leu
1               5                   10                  15

Ser Gln Lys Gly Tyr Ser Trp Ser Gln Phe Ser Asp Val Glu Glu Asn
            20                  25                  30

Arg Thr Glu Ala Pro Glu Gly Thr Glu Ser Glu Met Glu Thr Pro Ser
        35                  40                  45

Ala Ile Asn Gly Asn Pro Ser Trp His Leu Ala Asp Ser Pro Ala Val
    50                  55                  60

Asn Gly Ala Thr Gly His Ser Ser Ser Leu Asp Ala Arg Glu Val Ile
65                  70                  75                  80

Pro Met Ala Ala Val Lys Gln Ala Leu Arg Glu Ala Gly Asp Glu Phe
                85                  90                  95

Glu Leu Arg Tyr Arg Arg Ala Phe Ser Asp Leu Thr Ser Gln Leu His
            100                 105                 110

Ile Thr Pro Gly Thr Ala Tyr Gln Ser Phe Glu Gln Val Val Asn Glu
        115                 120                 125

Leu Phe Arg Asp Gly Val Asn Trp Gly Arg Ile Val Ala Phe Phe Ser
    130                 135                 140

Phe Gly Gly Ala Leu Cys Val Glu Ser Val Asp Lys Glu Met Gln Val
145                 150                 155                 160

Leu Val Ser Arg Ile Ala Ala Trp Met Ala Thr Tyr Leu Asn Asp His
                165                 170                 175

Leu Glu Pro Trp Ile Gln Glu Asn Gly Gly Trp Asp Thr Phe Val Glu
            180                 185                 190

Leu Tyr Gly Asn Asn Ala Ala Ala Glu Ser Arg Lys Gly Gln Glu Arg
        195                 200                 205

Phe Asn Arg Trp Phe Leu Thr Gly Met Thr Val Ala Gly Val Val Leu
    210                 215                 220

Leu Gly Ser Leu Phe Ser Arg Lys
225                 230
```

<210> SEQ ID NO 8

```
<211> LENGTH: 167
<212> TYPE: PRT
<213> ORGANISM: Homo sapiens

<400> SEQUENCE: 8

Phe Gln Ile Pro Glu Phe Glu Pro Ser Glu Gln Glu Asp Ser Ser
1               5                   10                  15

Ala Glu Arg Gly Leu Gly Pro Ser Pro Ala Gly Asp Gly Pro Ser Gly
            20                  25                  30

Ser Gly Lys His His Arg Gln Ala Pro Gly Leu Leu Trp Asp Ala Ser
        35                  40                  45

His Gln Gln Glu Gln Pro Thr Ser Ser Ser His His Gly Gly Ala Gly
    50                  55                  60

Ala Val Glu Ile Arg Ser Arg His Ser Ala Tyr Pro Ala Gly Thr Glu
65                  70                  75                  80

Asp Asp Glu Gly Met Gly Glu Pro Ser Pro Phe Arg Gly Arg Ser
                85                  90                  95

Arg Ala Ala Pro Pro Asn Leu Trp Ala Ala Gln Arg Tyr Gly Arg Glu
                100                 105                 110

Leu Arg Arg Met Ser Asp Glu Phe Val Asp Ser Phe Lys Lys Gly Leu
            115                 120                 125

Pro Arg Pro Lys Ser Ala Gly Thr Ala Thr Gln Met Arg Gln Ser Ser
        130                 135                 140

Ser Trp Thr Arg Val Phe Gln Ser Trp Trp Asp Arg Asn Leu Gly Arg
145                 150                 155                 160

Gly Ser Ser Ala Pro Ser Gln
                165

<210> SEQ ID NO 9
<211> LENGTH: 507
<212> TYPE: DNA
<213> ORGANISM: Homo sapiens

<400> SEQUENCE: 9
ggtagctttc agatcccgga atttgagccg agcgagcaag aggattcaag cagcgcggag      60
cgcggtctgg gtccgagccc ggcaggcgac ggtccgagcg gcagcggcaa gcatcaccgc     120
caggcgccag gcctgctgtg ggatgcatcg catcaacagg aacaaccgac gagcagcagc     180
catcatggtg gcgctggtgc ggttgagatt agatcgcgcc actccgcata tcctgccggc     240
accgaagatg acgaaggcat gggcgaggaa ccgagcccgt tccgtggccg tagccgtgct     300
gcaccgccga atctgtgggc cgcacagcgt tatggtcgcg agttgcgtcg catgtccgac     360
gagtttgttg actccttcaa gaaaggttta ccgcgtccga atctgccgg taccgcgacg     420 cagatgcgtc agagcagcag ctggacccgc gtgtttcaat cttggtggga tcgtaatctg     480
ggtcgtggta gcagcgcacc gagccaa                                         507

<210> SEQ ID NO 10
<211> LENGTH: 696
<212> TYPE: DNA
<213> ORGANISM: Homo sapiens

<400> SEQUENCE: 10
tctcagtcta accgcgaact ggtggtggac ttcctgtctt ataaactgag ccagaaaggc      60
tactcctgga gccagttcag cgacgtagag gagaaccgta ccgaagctcc tgaaggcacc     120
gagagcgaga tggaaacccc atccgcgatt aacggcaacc cgtcctggca cctggctgat     180
```

-continued

```
tctccggcgg taaacggcgc aactggtcat tctagctccc tggatgcacg tgaagtaatc    240
ccgatggccg cggttaaaca ggcgctgcgt gaagctggtg acgaatttga gctgcgctac    300
cgccgtgcat tttctgatct gacctcccag ctgcacatca cgccgggtac cgcataccaa    360
agcttcgaac aggtggttaa cgaactgttt cgtgacggcg tcaactgggg ccgcatcgtg    420
gcctttttct ctttcggcgg tgccctgtgc gtcgaatctg ttgacaaaga aatgcaggtt    480
ctggtgagcc gtattgcggc ttggatggca acttatctga cgatcacct ggaaccgtgg     540 atccaggaaa acggtggttg ggataccttc gttgaactgt acggtaacaa tgctgcggcg    600
gaatcccgta agggtcaaga acgtttcaat cgctggttcc tgaccggcat gactgttgct    660
ggtgtagttc tgctgggttc tctgttctcc cgtaaa                              696
```

<210> SEQ ID NO 11
<211> LENGTH: 366
<212> TYPE: PRT
<213> ORGANISM: Artificial Sequence
<220> FEATURE:
<223> OTHER INFORMATION: synthetic fusion protein; proS2-BclxL

<400> SEQUENCE: 11

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Ala Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala His Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr Gly Ser Ser Gln Ser Asn Arg Glu Leu Val Val Asp
130                 135                 140

Phe Leu Ser Tyr Lys Leu Ser Gln Lys Gly Tyr Ser Trp Ser Gln Phe
145                 150                 155                 160

Ser Asp Val Glu Glu Asn Arg Thr Glu Ala Pro Glu Gly Thr Glu Ser
                165                 170                 175

Glu Met Glu Thr Pro Ser Ala Ile Asn Gly Asn Pro Ser Trp His Leu
            180                 185                 190

Ala Asp Ser Pro Ala Val Asn Gly Ala Thr Gly His Ser Ser Ser Leu
        195                 200                 205

Asp Ala Arg Glu Val Ile Pro Met Ala Ala Val Lys Gln Ala Leu Arg
    210                 215                 220

Glu Ala Gly Asp Glu Phe Glu Leu Arg Tyr Arg Arg Ala Phe Ser Asp
225                 230                 235                 240

Leu Thr Ser Gln Leu His Ile Thr Pro Gly Thr Ala Tyr Gln Ser Phe
                245                 250                 255

Glu Gln Val Val Asn Glu Leu Phe Arg Asp Gly Val Asn Trp Gly Arg
            260                 265                 270
```

```
Ile Val Ala Phe Phe Ser Phe Gly Gly Ala Leu Cys Val Glu Ser Val
            275                 280                 285

Asp Lys Glu Met Gln Val Leu Val Ser Arg Ile Ala Ala Trp Met Ala
290                 295                 300

Thr Tyr Leu Asn Asp His Leu Glu Pro Trp Ile Gln Glu Asn Gly Gly
305                 310                 315                 320

Trp Asp Thr Phe Val Glu Leu Tyr Gly Asn Asn Ala Ala Glu Ser
                325                 330                 335

Arg Lys Gly Gln Glu Arg Phe Asn Arg Trp Phe Leu Thr Gly Met Thr
            340                 345                 350

Val Ala Gly Val Val Leu Leu Gly Ser Leu Phe Ser Arg Lys
            355                 360                 365

<210> SEQ ID NO 12
<211> LENGTH: 370
<212> TYPE: PRT
<213> ORGANISM: Artificial Sequence
<220> FEATURE:
<223> OTHER INFORMATION: synthetic cpProS2-BclxL fusion sequence

<400> SEQUENCE: 12

Met Leu Thr Ala Lys Phe Tyr Met Pro Lys Lys Ala Thr Glu Leu Lys
1               5                   10                  15

His Leu Gln Cys Leu Glu Glu Glu Leu Lys Pro Leu Glu Glu Val Leu
            20                  25                  30

Asn Leu Ala His Ser Lys Asn Phe His Phe Asp Pro Arg Asp Val Val
        35                  40                  45

Ser Asn Ile Asn Val Phe Val Leu Glu Leu Lys Gly Ser Glu Thr Thr
50                  55                  60

Phe Met Cys Glu Tyr Ala Asp Glu Thr Ala Thr Ile Val Glu Phe Leu
65                  70                  75                  80

Asn Arg Trp Ile Thr Phe Ser Gln Ser Ile Ile Ser Thr Leu Thr Gly
                85                  90                  95

Gly Asn Gly Gly Pro Thr Ser Ser Thr Lys Lys Thr Gln Leu Gln
            100                 105                 110

Leu Glu His Leu Leu Leu Asp Leu Gln Met Ile Leu Asn Gly Ile Asn
            115                 120                 125

Asn Tyr Lys Asn Pro Lys Leu Thr Gly Ser Ser Gln Ser Asn Arg Glu
130                 135                 140

Leu Val Val Asp Phe Leu Ser Tyr Lys Leu Ser Gln Lys Gly Tyr Ser
145                 150                 155                 160

Trp Ser Gln Phe Ser Asp Val Glu Glu Asn Arg Thr Glu Ala Pro Glu
                165                 170                 175

Gly Thr Glu Ser Glu Met Glu Thr Pro Ser Ala Ile Asn Gly Asn Pro
            180                 185                 190

Ser Trp His Leu Ala Asp Ser Pro Ala Val Asn Gly Ala Thr Gly His
        195                 200                 205

Ser Ser Ser Leu Asp Ala Arg Glu Val Ile Pro Met Ala Ala Val Lys
210                 215                 220

Gln Ala Leu Arg Glu Ala Gly Asp Glu Phe Glu Leu Arg Tyr Arg Arg
225                 230                 235                 240

Ala Phe Ser Asp Leu Thr Ser Gln Leu His Ile Thr Pro Gly Thr Ala
                245                 250                 255

Tyr Gln Ser Phe Glu Gln Val Val Asn Glu Leu Phe Arg Asp Gly Val
            260                 265                 270
```

```
Asn Trp Gly Arg Ile Val Ala Phe Ser Phe Gly Ala Leu Cys
            275                 280                 285

Val Glu Ser Val Asp Lys Glu Met Gln Val Leu Val Ser Arg Ile Ala
    290                 295                 300

Ala Trp Met Ala Thr Tyr Leu Asn Asp His Leu Glu Pro Trp Ile Gln
305                 310                 315                 320

Glu Asn Gly Gly Trp Asp Thr Phe Val Glu Leu Tyr Gly Asn Asn Ala
                325                 330                 335

Ala Ala Glu Ser Arg Lys Gly Gln Glu Arg Phe Asn Arg Trp Phe Leu
            340                 345                 350

Thr Gly Met Thr Val Ala Gly Val Val Leu Leu Gly Ser Leu Phe Ser
            355                 360                 365

Arg Lys
    370

<210> SEQ ID NO 13
<211> LENGTH: 301
<212> TYPE: PRT
<213> ORGANISM: Artificial Sequence
<220> FEATURE:
<223> OTHER INFORMATION: synthetic proS2-Bad fusion sequence

<400> SEQUENCE: 13

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Ala Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr Gly Ser Phe Gln Ile Pro Glu Phe Glu Pro Ser Glu
130                 135                 140

Gln Glu Asp Ser Ser Ser Ala Glu Arg Gly Leu Gly Pro Ser Pro Ala
145                 150                 155                 160

Gly Asp Gly Pro Ser Gly Ser Gly Lys His His Arg Gln Ala Pro Gly
                165                 170                 175

Leu Leu Trp Asp Ala Ser His Gln Gln Glu Gln Pro Thr Ser Ser Ser
            180                 185                 190

His His Gly Gly Ala Gly Ala Val Glu Ile Arg Ser Arg His Ser Ala
            195                 200                 205

Tyr Pro Ala Gly Thr Glu Asp Asp Glu Gly Met Gly Glu Glu Pro Ser
    210                 215                 220

Pro Phe Arg Gly Arg Ser Arg Ala Ala Pro Pro Asn Leu Trp Ala Ala
225                 230                 235                 240

Gln Arg Tyr Gly Arg Glu Leu Arg Arg Met Ser Asp Glu Phe Val Asp
                245                 250                 255
```

```
Ser Phe Lys Lys Gly Leu Pro Arg Pro Lys Ser Ala Gly Thr Ala Thr
            260                 265                 270

Gln Met Arg Gln Ser Ser Ser Trp Thr Arg Val Phe Gln Ser Trp Trp
        275                 280                 285

Asp Arg Asn Leu Gly Arg Gly Ser Ser Ala Pro Ser Gln
    290                 295                 300
```

<210> SEQ ID NO 14
<211> LENGTH: 305
<212> TYPE: PRT
<213> ORGANISM: Artificial Sequence
<220> FEATURE:
<223> OTHER INFORMATION: synthetic cpProS2-Bad fusion sequence

<400> SEQUENCE: 14

```
Met Leu Thr Ala Lys Phe Tyr Met Pro Lys Lys Ala Thr Glu Leu Lys
1               5                   10                  15

His Leu Gln Cys Leu Glu Glu Glu Leu Lys Pro Leu Glu Glu Val Leu
            20                  25                  30

Asn Leu Ala His Ser Lys Asn Phe His Phe Asp Pro Arg Asp Val Val
        35                  40                  45

Ser Asn Ile Asn Val Phe Val Leu Glu Leu Lys Gly Ser Glu Thr Thr
    50                  55                  60

Phe Met Cys Glu Tyr Ala Asp Glu Thr Ala Thr Ile Val Glu Phe Leu
65                  70                  75                  80

Asn Arg Trp Ile Thr Phe Ser Gln Ser Ile Ile Ser Thr Leu Thr Gly
                85                  90                  95

Gly Asn Gly Gly Pro Thr Ser Ser Ser Thr Lys Lys Thr Gln Leu Gln
            100                 105                 110

Leu Glu His Leu Leu Leu Asp Leu Gln Met Ile Leu Asn Gly Ile Asn
        115                 120                 125

Asn Tyr Lys Asn Pro Lys Leu Thr Gly Ser Phe Gln Ile Pro Glu Phe
    130                 135                 140

Glu Pro Ser Glu Gln Glu Asp Ser Ser Ser Ala Glu Arg Gly Leu Gly
145                 150                 155                 160

Pro Ser Pro Ala Gly Asp Gly Pro Ser Gly Ser Gly Lys His His Arg
                165                 170                 175

Gln Ala Pro Gly Leu Leu Trp Asp Ala Ser His Gln Gln Glu Gln Pro
            180                 185                 190

Thr Ser Ser Ser His His Gly Gly Ala Gly Ala Val Glu Ile Arg Ser
        195                 200                 205

Arg His Ser Ala Tyr Pro Ala Gly Thr Glu Asp Asp Glu Gly Met Gly
    210                 215                 220

Glu Glu Pro Ser Pro Phe Arg Gly Arg Ser Arg Ala Ala Pro Pro Asn
225                 230                 235                 240

Leu Trp Ala Ala Gln Arg Tyr Gly Arg Glu Leu Arg Arg Met Ser Asp
                245                 250                 255

Glu Phe Val Asp Ser Phe Lys Lys Gly Leu Pro Arg Pro Lys Ser Ala
            260                 265                 270

Gly Thr Ala Thr Gln Met Arg Gln Ser Ser Ser Trp Thr Arg Val Phe
        275                 280                 285

Gln Ser Trp Trp Asp Arg Asn Leu Gly Arg Gly Ser Ser Ala Pro Ser
    290                 295                 300

Gln
305
```

<210> SEQ ID NO 15
<211> LENGTH: 82
<212> TYPE: PRT
<213> ORGANISM: Artificial Sequence
<220> FEATURE:
<223> OTHER INFORMATION: synthetic ubiquitin linker

<400> SEQUENCE: 15

```
Gly Gly Gly Ser Met Gln Ile Phe Val Arg Thr Leu Thr Gly Arg Thr
1               5                   10                  15
Ile Thr Leu Glu Val Glu Pro Ser Asp Thr Ile Glu Asn Val Arg Ala
            20                  25                  30
Arg Ile Gln Asp Arg Glu Gly Ile Pro Pro Asp Gln Gln Arg Leu Ile
        35                  40                  45
Phe Ala Gly Arg Gln Leu Glu Asp Gly Arg Thr Leu Ser Asp Tyr Asn
    50                  55                  60
Ile Gln Arg Glu Ser Thr Leu His Leu Val Leu Arg Leu Arg Gly Gly
65                  70                  75                  80
Gly Ser
```

<210> SEQ ID NO 16
<211> LENGTH: 927
<212> TYPE: DNA
<213> ORGANISM: Artificial Sequence
<220> FEATURE:
<223> OTHER INFORMATION: synthetic bpproS2-Bad

<400> SEQUENCE: 16

```
atgccgacct ctagctctac caaaaagacg caattgcaac tggagcacct tttgctggat      60
ctgcagatga ttctgaatgg tatcaacaac tacaagaacc cgaaactgac ccgtatgctg     120
acggccaaat tctacatgcc taagaaagcg accgagctga agcacttgca atgcctggaa     180
gaagaactga agccgctgga agaagtcctg aatctggcgc agtccaaaaa cttccacttt     240
gacccacgtg atgtggttag caacatcaat gtctttgtcc tggagctcaa aggtagcgag     300
actaccttca tgtgtgagta cgcggacgaa actgcgacca ttgtggagtt cctgaaccgt     360
tggatcacgt tcagccagtc catcattagc acgctgaccg tagctttca gatcccggaa     420
tttgagccga gcgagcaaga ggattcaagc agcgcggagc gcggtctggg tccgagcccg     480
gcaggcgacg tccgagcgg cagcggcaag catcaccgcc aggcgccagg cctgctgtgg     540
gatgcatcgc atcaacagga acaaccgacg agcagcagcc atcatggtgg cgctggtgcg     600
gttgagatta gatcgcgcca ctccgcatat cctgccggca ccgaagatga cgaaggcatg     660
ggcgaggaac cgagcccgtt ccgtggccgt agccgtgctg caccgccgaa tctgtgggcc     720
gcacagcgtt atggtcgcga gttgcgtcgc atgtccgacg agtttgttga ctccttcaag     780
aaaggtttac cgcgtccgaa atctgccggt accgcgacgc agatgcgtca gagcagcagc     840
tggacccgcg tgtttcaatc ttggtgggat cgtaatctgg gtcgtggtag cagcgcaccg     900
agccaacacc accatcacca tcactaa                                         927
```

<210> SEQ ID NO 17
<211> LENGTH: 308
<212> TYPE: PRT
<213> ORGANISM: Artificial Sequence
<220> FEATURE:
<223> OTHER INFORMATION: synthetic proS2-Bad

<400> SEQUENCE: 17

```
Met Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Phe Gln Ile Pro Glu Phe Glu Pro Ser
    130                 135                 140

Glu Gln Glu Asp Ser Ser Ala Glu Arg Gly Leu Gly Pro Ser Pro
145                 150                 155                 160

Ala Gly Asp Gly Pro Ser Gly Ser Gly Lys His His Arg Gln Ala Pro
                165                 170                 175

Gly Leu Leu Trp Asp Ala Ser His Gln Gln Glu Gln Pro Thr Ser Ser
            180                 185                 190

Ser His His Gly Gly Ala Gly Ala Val Glu Ile Arg Ser Arg His Ser
        195                 200                 205

Ala Tyr Pro Ala Gly Thr Glu Asp Asp Glu Gly Met Gly Glu Glu Pro
    210                 215                 220

Ser Pro Phe Arg Gly Arg Ser Arg Ala Ala Pro Pro Asn Leu Trp Ala
225                 230                 235                 240

Ala Gln Arg Tyr Gly Arg Glu Leu Arg Arg Met Ser Asp Glu Phe Val
                245                 250                 255

Asp Ser Phe Lys Lys Gly Leu Pro Arg Pro Lys Ser Ala Gly Thr Ala
            260                 265                 270

Thr Gln Met Arg Gln Ser Ser Trp Thr Arg Val Phe Gln Ser Trp
        275                 280                 285

Trp Asp Arg Asn Leu Gly Arg Gly Ser Ser Ala Pro Ser Gln His His
    290                 295                 300

His His His His
305

<210> SEQ ID NO 18
<211> LENGTH: 4
<212> TYPE: PRT
<213> ORGANISM: Artificial Sequence
<220> FEATURE:
<223> OTHER INFORMATION: synthetic cleavable linker

<400> SEQUENCE: 18

Ile Leu Gly Arg
1

<210> SEQ ID NO 19
<211> LENGTH: 5
<212> TYPE: PRT
<213> ORGANISM: Artificial Sequence
<220> FEATURE:
```

```
<223> OTHER INFORMATION: synthetic cleavable linker

<400> SEQUENCE: 19

Asp Asp Asp Asp Lys
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic cleavable linker

<400> SEQUENCE: 20

Leu Val Pro Arg Gly
1               5
```

INTERLEUKIN-2 FUSION PROTEINS AND USES THEREOF

CROSS REFERENCES TO RELATED APPLICATIONS

The present application is a division of U.S. application Ser. No. 16/992,068, filed on Mar. 24, 2016, which is a 371 of International Application No. PCT/CA2014/05091, filed on Sep. 24, 2014, which claims priority to U.S. Provisional Application No. 61/881,931, filed on Sep. 24, 2013, all of which are hereby incorporated by reference in their entirety.

FIELD OF INVENTION

The present invention relates to interleukin-2 fusion proteins. More specifically, the invention provides, in part, fusion proteins that include an interleukin-2 protein moiety joined to a Bcl-2 family member protein moiety.

REFERENCE TO SEQUENCE LISTING

This invention incorporated by reference the Sequence Listing text copy submitted herewith, which was created on Aug. 14, 2020, entitled 117802-5004-US01_Sequence_Listing.txt which is 28 kilobytes in size.

BACKGROUND OF THE INVENTION

Interleukin-2 (IL-2) is a pluripotent cytokine produced primarily by activated CD4$^+$ T cells, which plays a crucial role in producing a normal immune response. IL-2 promotes proliferation and expansion of activated T lymphocytes, potentiates B cell growth, and activates monocytes and natural killer cells IL-2 is the ligand for the interleukin 2 receptor alpha (IL-2Rα or CD25; also known as "Tac" antigen) and the interleukin 2 receptor beta (IL-2Rβ or CD 122) and interleukin 2 receptor gamma (IL-2Rγ or CD 132; common gamma chain), which are expressed coordinately.

The IL-2Rα binds IL-2 with a $K_d$ of about $10^{-8}$ M, and is also known as the "low affinity" IL-2 receptor; binding of IL-2 to cells expressing only the IL-2Rα does not lead to any detectable biologic response.

Most cells, for example, resting T cells are insensitive to IL-2 since they only express the IL-2Rβ and the IL-2Rγ. Upon antigen receptor-mediated T cell activation, the IL-2Rα is rapidly expressed. Once the IL-2Rα binds IL-2, it then sequentially engages the IL-2Rβ and the IL-2Rγ, leading to signal transduction and IL-2-mediated growth stimulation.

Recombinant human IL-2 (Proleukin®, aldesleukin) is approved as an immunotherapy to treat metastatic melanoma and metastatic kidney cancer Proleukin® has been used for over 15 years in the treatment of cancer and has shown complete or partial response rates of around 15% in patients with metastatic melanoma or kidney cancer. However, Proleukin causes side effects that lead to pulmonary edema and liver damage.

Ontak® (denileukin diftitox), a fusion protein consisting of IL-2 as the targeting ligand and a modified bacterial toxin as the cell-killing payload is approved in the United States for the treatment of cutaneous T-cell lymphoma (CTCL). While Ontak is widely considered to be an effective drug to treat CTCL, it has major safety issues, resulting in limited use in the U.S. and no ex-U.S. approvals. Since its approval in 1999 for CTCL, trials in rheumatoid arthritis, psoriasis, lung cancer and other indications have showed encouraging signs of efficacy for Ontak but have been abandoned due to the severity of toxic side effects. Accordingly, the use of IL-2 as an antineoplastic agent has been limited by the serious toxicides that accompany the doses necessary for a tumor response.

Circularly permuted molecules are those in which the termini of a linear molecule (e.g., ligand) have been joined together, either directly or via a linker, to produce a circular molecule, after which the circular molecule is opened at another location to produce a new linear molecule with termini different from the termini of the original molecule. Circularly permuted variants of IL-2 have been described in, for example, U.S. Pat. No. 6,011,002, issued Jan. 4, 2000, to Pastan et al.

Programmed cell death or "apoptosis," is a common phenomenon in the development of animal cells and is both positively and negatively regulated in addition to its involvement in lymphoid system development and overall cell population homeostasis, apoptosis also plays a significant role in various diseases and injuries resulting from aberrant regulation of apoptotic pathways. Conversely, aberrant suppression of apoptosis can result in hyperproliferation of cells, leading to cancer and other hyperproliferative disorders.

Apoptosis is regulated by a number of proteins, including members of the Bcl-2 family. Bcl-2 was one of the first proteins identified as regulating apoptosis (Cleary et al., Cell 47:19-28, 1986; Tsujtmoto and Croce, Proc. Natl. Acad. Sci. USA 83:5214-5218, 1986). Since its discovery, several Bcl-2-related proteins ("Bcl-2 family proteins" or "Bcl-2 family members") have been identified as regulators of apoptosis (White, Genes Dev. 10:1-15, 1996; Yang et al., Cell 80:285-291, 1995).

Several therapeutic agents for treatment of cancer, etc. have been explored but exhibit limitations that restrict their use in the clinic. For example, many chemotherapeutic agents act by inducing apoptosis in proliferating neoplastic cells, but their therapeutic value is limited by the extent to which they are toxic to normal cells. Treatment with standard apoptosis inhibitory molecules, for instance peptide-type caspase inhibitors (e.g., DEVD-type), has proven unsatisfactory for clinical work due to low membrane permeability of these inhibitors.

Targeted immunotoxins (genetic or biochemical fusions between a toxic molecule, for instance a bacterial toxin, and a targeting domain derived, typically from an antibody molecule) have been proposed in attempts to selectively eliminate cancer cells. For example, diphtheria toxin (DT) variants have been generated and tested for their ability to selectively kill cancer cells (Thorpe et al., Nature 271:752-755, 1978; Laske et al., Nature Medicine 3:1362-1368, 1997). Similarly, *Pseudomonas* exotoxin (PE) fusion proteins have been investigated as potential cancer therapeutics (Kreitman and Pastan, Blood 90:252-259, 1997; Shimamura et al., Cancer Res. 67:9903-9912; 2007). DT-BclxL fusion proteins have been tested for their ability to block apoptosis induced by staurosporin, γ-irradiation, and poliovirus in a variety of cells types (Youle et al., Proc Natl Acad Sci. 96:9563-9567). Granulocyte-macrophage colony-stimulating factor BclxL (GM-CSF-BclxL) fusion proteins have been shown to increase the proliferation of human monocytes, and protect cells from induced cell death (Youle et al., JBC 282(15):11246-11254).

SUMMARY OF THE INVENTION

The present invention relates to interleukin-2 fusion proteins. More specifically, the invention provides, in part, fusion proteins that include an interleukin-2 protein moiety joined to a Bcl-2 family member protein moiety and uses thereof.

In one aspect, the invention provides a fusion protein including an interleukin-2 (IL-2) and a Bcl-2 family polypeptide. In some embodiments, the Bcl-2 family polypeptide may be a pro-apoptotic Bcl-2 family polypeptide comprising a BH3 domain (such as Bad, Bik/Nbk, Bid, Bim/Bod, Hrk, Bak or Bax). The BH3 domain may further include a mutation that reduces phosphorylation. The pro-apoptotic Bcl-2 family polypeptide including a BH3 domain that further includes a mutation that reduces phosphorylation may be a Bad polypeptide. The fusion protein may be capable of inhibiting cell survival, inhibiting cell proliferation, or enhancing cell death or apoptosis of a target cell expressing an IL-2R.

In some embodiments, the Bcl-2 family polypeptide may be an anti-apoptotic Bcl-2 family polypeptide (such as Bcl-$x_L$, Bcl-w or Bcl-2). The fusion protein may be capable of enhancing cell survival, enhancing cell proliferation, or inhibiting cell death or apoptosis of a target cell expressing an IL-2R.

In some embodiments, the IL-2 may be circularly permuted (cp). In some embodiments, the IL-2 may be a mutant IL-2 that has increased selectivity for IL-2Rβ relative to native IL-2, or that has increased selectivity for IL-2Rγ relative to native IL-2, or disrupts the association between IL-2Rβ and IL-2Rγ.

In some embodiments, the fusion protein may further include a linker. The linker may have the sequence GS or may be a ubiquitin or ubiquitin variant molecule.

In some aspects, there is provided a nucleic acid molecule encoding a fusion protein as described herein, or a vector including the nucleic acid molecule, or a host cell including the vector.

In some aspects, there is provided a pharmaceutical composition including a fusion protein as described herein, a nucleic acid molecule encoding the fusion protein, or a vector including the nucleic acid molecule, or a host cell including the vector.

In some aspects, there is provided a method of inducing cell death by administering a fusion protein including a pro-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of inducing cell death by contacting a target cell that expresses an IL-2R with a fusion protein including a pro-apoptotic Bcl-2 family polypeptide, a nucleic acid molecule encoding the fusion protein, or a vector including the nucleic acid molecule.

In some aspects, there is provided a method of treating cancer by administering: a fusion protein including a pro-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of treating cancer by contacting a neoplastic cell that expresses an IL-2R with a fusion protein including a pro-apoptotic Bcl-2 family polypeptide, a nucleic acid molecule encoding the fusion protein, or a vector including the nucleic acid molecule.

In some aspects, there is provided a method of treating cancer by contacting a non-malignant cell that expresses an IL-2R in a tumour microenvironment with a fusion protein including a pro-apoptotic Bcl-2 family polypeptide, a nucleic acid molecule encoding the fusion protein, or a vector including the nucleic acid molecule.

In some aspects, there is provided a method of treating cancer by contacting an immune cell that expresses an IL-2R with a fusion protein including a pro-apoptotic Bcl-2 family polypeptide, a nucleic acid molecule encoding the fusion protein, or a vector including the nucleic acid molecule. In some embodiments, the immune cell is a natural killer cell and the fusion protein is an anti-apoptotic Bcl-2 family polypeptide. In alternative embodiments, the immune cell is a regulatory T cell and the fusion protein is a pro-apoptotic Bcl-2 family polypeptide.

In some aspects, there is provided a method of treating an autoimmune disorder by administering a fusion protein including a pro-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of stimulating cell proliferation by administering a fusion protein including an anti-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of stimulating cell proliferation by contacting a target cell that expresses an IL-2R with a fusion protein including an anti-apoptotic Bcl-2 family polypeptide, a nucleic acid molecule encoding the fusion protein, or a vector including the nucleic acid molecule.

In some aspects, there is provided a method of enhancing an immune response by administering a fusion protein including an anti-apoptotic Bcl-2 family polypeptide, a nucleic acid molecule encoding the fusion protein, or a vector including the nucleic acid molecule, or a host cell including the vector, to a subject in need thereof.

In some aspects, there is provided a method of enhancing an immune response by contacting a target cell that expresses an IL-2R with a fusion protein including an anti-apoptotic Bcl-2 family polypeptide, a nucleic acid molecule encoding the fusion protein, or a vector including the nucleic acid molecule.

In some aspects, there is provided a method of propagating or expanding engineered T cells for use in adoptive cell transfer therapy or chimeric antigen receptor (CAR) therapy comprising contacting the engineered T cell with a fusion protein according to the invention, a nucleic acid molecule encoding the fusion protein, or a vector including the nucleic acid molecule.

In some aspects, there is provided a use of a fusion protein according to the invention, a nucleic acid molecule encoding the fusion protein, or a vector including the nucleic acid molecule for inducing cell death, treating cancer, treating an autoimmune disorder, stimulating cell proliferation, enhancing an immune response, or propagating or expanding engineered T cells for use in adoptive cell transfer therapy or chimeric antigen receptor (CAR) therapy, in a cell or in a subject in need thereof.

In various embodiments of the alternative aspects, the subject may be a human.

This summary does not necessarily describe all features of the invention.

BRIEF DESCRIPTION OF THE DRAWINGS

These and other features of the invention will become more apparent from the following description in which reference is made to the appended drawings wherein:

FIGS. 2A-2B show the nucleic acid sequence (A) and amino acid (B) sequence of proS2-BAD.

DETAILED DESCRIPTION

Figure 1:
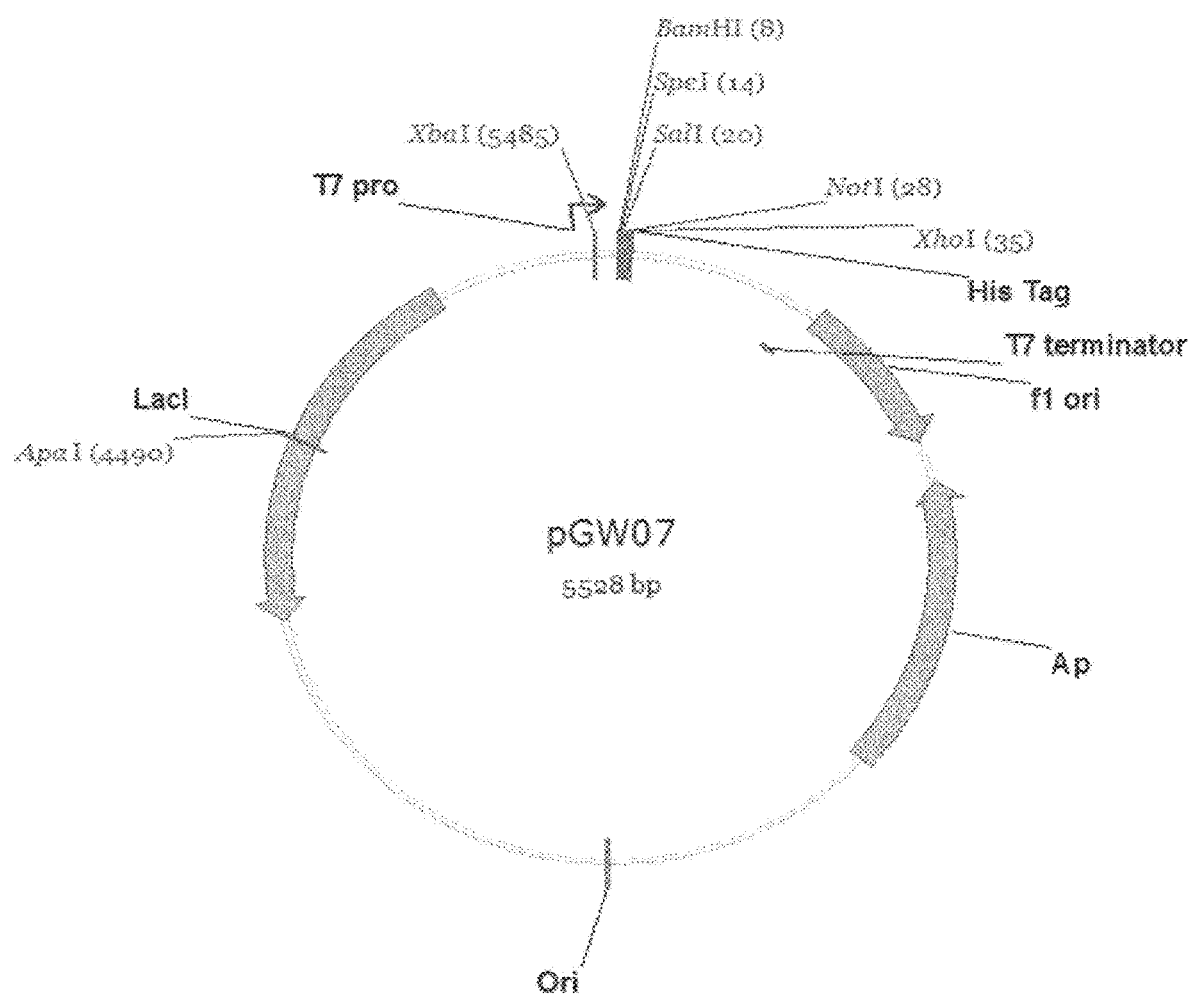
FIG. 1 is an illustration of a pGW07 *E. coli* expression vector.

The present disclosure provides, in part, fusion proteins including an IL-2 protein joined to a Bcl-2 family protein and uses thereof.

IL-2 Proteins

IL-2 proteins include native IL-2 proteins, as well as variant IL-2 proteins. A "native" or "wild type" IL-2 sequence, as used herein, refers to a human IL-2 sequence (e.g., Accession No. NP_000577.2), whether purified from natural sources or made using recombinant techniques. In some embodiments, a wild type IL-2 sequence includes the Proleukin® (aldesleukin) sequence:

```
                                        (SEQ ID NO: 1)
PTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGS
ETTFMCEYADETATIVEFLNRWITFAQSIISTLT.
```

In some embodiments, IL-2 proteins that can be used in the fusion proteins of the present disclosure are variant IL-2 proteins that have increased selectivity for IL-2Rβ relative to native IL-2, or that have increased selectivity for IL-2Rγ relative to native IL-2, or that disrupt the association between IL-2Rβ and IL-2Rγ as described, for example, in WO 2012/088446.

In some embodiments, IL-2 proteins that can be used in the fusion proteins of the present disclosure include the amino acid sequence as follows:

```
                                        (SEQ ID NO: 2)
PTSSSTKKTQLQLEHLLLDLQMILNGINNYKNPKLTRMLTFKFYMPKKA
TELKHLQCLEEELKPLEEVLNLAHSKNFHFDPRDVVSNINVFVLELKGS
ETTFMCEYADETATIVEFLNRWITFSQSIISTLT.
```

In some embodiments, IL-2 proteins that can be used in the fusion proteins of the present disclosure include the amino acid sequence as follows:

```
                                        (SEQ ID NO: 23)
PTSSSTKKTQLQLEHLLLDLQMILNGINNYKNPKLTRMLTAKFYMPKKA
TELKHLQCLEEELKPLEEVLNLAHSKNFHFDPRDVVSNINVFVLELKGS
ETTFMCEYADETATIVEFLNRWITFSQSIISTLT (ProS2).
```

In some embodiments, IL-2 proteins that disrupt the association between IL-2Rβ and IL-2Rγ include the following substitutions: 18R, 22E, 80F, 81D, 85V, 86I, 89I, 93V and 126T; or 18R, 22E, 74S, 80L, 81T, 85V, 86I, 89I, 92F, 93V and 126T; or 18R, 22E, 80F, 81D, 85V, 86V, 89I, 92F, 93V and 126T, compared to wild type IL-2.

In some embodiments, IL-2 proteins that can be used in the fusion proteins of the present disclosure are circularly permuted (cp), as described in, for example, U.S. Pat. No. 6,011,002, issued Jan. 4, 2000, to Pastan et al.

In alternative embodiments, a cpIL-2 protein that can be used in the fusion proteins of the present disclosure includes a protein as follows:

```
                                        (SEQ ID NO: 4)
MLTAKFYMPKKATELKHLQCLEEELKPLEEVLNLAHSKNFHFDPRDVVS
NINVFVLELKGSETTFMCEYADETATIVEFLNRWITFSQSIISTLT
GGNGGPTSSSTKKTQLQLEHLLLDLQMILNGINNYKNPKLT
(cpProS2).
```

Exemplary IL-2 proteins that can be used in the fusion proteins of the present disclosure include those described herein, as well as sequences having at least 80% sequence identity, at least 85%, at least 90%, at least 95%, at least 98% or even at least 99% sequence identity to native IL-2 ("variant IL-2 proteins"), as long as the variant IL-2 protein retains the ability to bind the IL-2 receptor, or has increased selectivity for IL-2Rβ relative to native IL-2, or that have increased selectivity for IL-2Rγ relative to native IL-2, as described, for example, in WO 2012/088446 or in Levin et al., Nature 484:529-533,2012, or retains a desired biological activity.

It is to be understood that IL-2 proteins according to the present disclosure include fragments that can be smaller than the native amino acid IL-2 protein, as long as the IL-2 protein fragment retains the ability to bind the IL-2 receptor, or retains increased selectivity for IL-2Rβ relative to native IL-2, or increased selectivity for IL-2Rγ relative to native IL-2, as described, for example, in WO 2012/088446 or in Levin et al., Nature 484:529-533, 2012), or retains a desired biological activity, whether as a fragment of the native sequence or in a cp form or fragment thereof.

It is also to be understood that the present disclosure encompasses nucleic acid molecules that encode an IL-2 protein as described herein or known in the art.

Exemplary IL-2 nucleic acid molecules include:

```
                                        (SEQ ID NO: 5)
ATGCCGACCTCTAGCTCTACCAAAAAGACGCAATTGCAACTGGAGCACC
TTTTGCTGGATCTGCAGATGATTCTGAATGGTATCAACAACTACAAGAA
CCCGAAACTGACCCGTATGCTGACGGCCAAATTCTACATGCCTAAGAAA
GCGACCGAGCTGAAGCACTTGCAATGCCTGGAAGAAGAACTGAAGCCGC
TGGAAGAAGTCCTGAATCTGGCGCAGTCCAAAAACTTCCACTTTGACCC
ACGTGATGTGGTTAGCAACATCAATGTCTTTGTCCTGGAGCTCAAAGGT
AGCGAGACTACCTTCATGTGTGAGTACGCGGACGAAACTGCGACCATTG
TGGAGTTCCTGAACCGTTGGATCACGTTCAGCCAGTCCATCATTAGCAC
GCTGACC (proS2);
``` and

```
                                        (SEQ ID NO: 6)
ATGCTGACCGCGAAATTCTACATGCCAAAGAAAGCGACCGAGCTGAAAC
ACTTGCAATGCCTGGAAGAAGAGTTGAAGCCGCTGGAAGAAGTCCTGAA
TCTGGCCCAGTCCAAGAACTTTCACTTCGATCCGCGTGACGTTGTCTCT
AACATCAATGTGTTTGTCCTGGAGCTGAAGGGTAGCGAAACCACGTTCA
TGTGTGAGTACGCGGACGAAACTGCGACGATTGTGGAGTTCCTGAATCG
TTGGATTACGTTCTCTCAGTCCATTATCAGCACGCTGACCGGTGGTAAT
GGTGGCCCTACCAGCAGCAGCACCAAGAAAACTCAGCTGCAACTGGAGC
```

-continued

ACTTGCTGCTGGATCTGCAAATGATCCTCAACGGTATCAACAACTACAA

AAACCCGAAACTTACC (cpproS2).

BCL-2 Family Proteins

Bcl-2-related proteins or polypeptides ("Bcl-2 family proteins" or "Bcl-2 family members") are involved in regulation of apoptosis. Bcl-2 family proteins fall into two distinct categories those that inhibit cell death (the "anti-apoptotic" Bcl-2 family proteins) and those that enhance cell death (the "pro-apoptotic" Bcl-2 family proteins). Bcl-2 family proteins share one to four conserved Bcl-2 homology (BH) domains, designated BH1, BH2, BH3, and BH4.

Anti-apoptotic Bcl-2 family proteins include Bcl-2 itself, Bcl-$x_L$ (Boise et al., Cell 74:597-608, 1993; e.g., GenBank Accession No. Q07817; GenBank Accession No. Z23115), Bcl-w, etc. In some embodiments, a Bcl-$x_L$ protein that can be used in the fusion proteins according to the present disclosure includes a sequence as follows:

(SEQ ID NO: 7)
SQSNRELWDFLSYKLSQKGYSWSQFSDVEENRTEAPEGTESEMETPSAI

NGNPSWHLADSPAVNGATGHSSSLDAREVIPMAAVKQALREAGDEFELR

YRRAFSDLTSQLHITPGTAYQSFEQVVNELFRDGVNWGRIVAFFSFGGA

LCVESVDKEMQVLVSRIAAWMATYLNDHLEPWIQENGGWDTFVELYGNN

AAAESRKGQERFNRWFLTGMTVAGVVLLGSLFSRK.

In some embodiments, an anti-apoptotic Bcl-2 family protein includes at least a fragment of a Bcl-2 family member, where the anti-apoptotic Bcl-2 family protein or fragment is capable of enhancing cell survival, enhancing cell proliferation, or inhibiting cell death or apoptosis. By "enhancing cell survival" is meant increasing (e.g., by at least 10%, 20%, 30%, or by as much as 50%, 75%, 85% or 90% or more) the probability that a cell at risk of cell death will survive. By "enhancing cell proliferation" is meant increasing (e.g., by at least 10%, 20%, 30%, or by as much as 50%, 75%, 85% or 90% or more) the growth or proliferation of a cell. By "inhibiting cell death or apoptosis" is meant reducing (e.g., by at least 10%, 20%, 30%, or by as much as 50%, 75%, 85% or 90% or more) the probability that a cell at risk of cell death will undergo apoptotic, necrotic, or any other form of cell death. Suitable assays for measuring the enhancement of cell survival, enhancement of cell proliferation, or inhibition of cell death or apoptosis are described herein or known in the art.

Pro-apoptotic Bcl-2 family proteins include those having a BH3 domain, such as Bad (e.g., Accession no: NPH6784 or CAG46757), Bik/Nbk (e.g., Accession no: CAG30276), Bid (e.g., Accession no: CAG28531), Bim/Bod (e.g., Accession no: NP619527), Hrk, Bak or Bax). In some embodiments, pro-apoptotic Bcl-2 family proteins that can be used in the fusion proteins according to the present disclosure are mutated (for example at serine residues e.g., serine to alanine mutations) to prevent phosphorylation.

Bad, Bcl-2-associated agonist of cell death, is a regulator of programmed cell death (apoptosis). Bad positively regulates cell apoptosis by forming heterodimers with Bcl-$x_L$ and Bcl-2, and reversing their death repressor activity. Proapoptotic activity of Bad is regulated through its phosphorylation. Exemplary Bad proteins that can be used in the fusion proteins of the present disclosure include those in GenBank Accession Nos. CAG46757; AAH01901.1; and CAG46733.1, as well as those sequences provided in U.S. Pat. No. 6,737,511 (sequences herein incorporated by reference) and described herein, as well as sequences having at least 80% sequence identity, at least 85%, at least 90%, at least 95%, at least 98% or even at least 99% sequence identity to such sequences, as long as the variant retains or has enhanced biological activity of the native Bad protein. In some embodiments, a Bad protein that can be used in the fusion proteins according to the present disclosure contains serine mutations at positions 112 and/or 136 to reduce phosphorylation. In some embodiments, a Bad protein that can be used in the fusion proteins according to the present disclosure contains serine to alanine mutations at positions 112 and/or 136 to reduce phosphorylation. In some embodiments, a Bad protein that can be used in the fusion proteins according to the present disclosure includes a sequence as follows:

(SEQ ID NO: 8)
FQIPEFEPSEQEDSSSAERGLGPSPAGDGPSGSGKHHRQAPGLLWDASH

QQEQPTSSSHHGGAGAVEIRSRHS<u>A</u>YPAGTEDDEGMGEEPSPFRGRSR<u>A</u>

APPNLWAAQRYGRELRRMSDEFVDSFKKGLPRPKSAGTATQMRQSSSWT

RVFQSWWDRNLGRGSSAPSQ.

In some embodiments, a pro-apoptotic Bec-2 family protein includes at least a fragment of a Bcl-2 family member, where the pro-apoptotic Bcl-2 family protein or fragment is capable of inhibiting cell survival, inhibiting cell proliferation, or enhancing cell death or apoptosis. By "inhibiting cell survival" is meant decreasing (e.g., by at least 10%, 20%, 30%, or by as much as 50%, 75%, 85% or 90% or more) the probability that a cell at risk of cell death will survive. By "inhibiting cell proliferation" is meant decreasing (e.g., by at least 10%, 20%, 30%, or by as much as 50%, 75%, 85% or 90% or more) the growth or proliferation of a cell. By "enhancing cell death or apoptosis" is meant increasing (e.g., by at least 10%, 20%, 30%, or by as much as 50%, 75%, 85% or 90% or more) the probability that a cell at risk of cell death will undergo apoptotic, necrotic, or any other form of cell death. Suitable assays for measuring the inhibition of cell survival, inhibition of cell proliferation, or enhancement of cell death or apoptosis are described herein or known in the art.

It is also to be understood that the present disclosure encompasses nucleic acid molecules that encode a Bcl-2 family member as described herein.

Exemplary Bcl-2 family member nucleic acid molecules include:

(SEQ ID NO: 9)
GGTAGCTTTCAGATCCCGGAATTTGAGCCGAGCGAGCAAGAGGATTCAA

GCAGCGCGGAGCGCGGTCTGGGTCCGAGCCCGGCAGGCGACGGTCCGAG

CGGCAGCGGCAAGCATCACCGCCAGGCGCCAGGCCTGCTGTGGGATGCA

TCGCATCAACAGGAACAACCGACGAGCAGCAGCCATCATGGTGGCGCTG

GTGCGGTTGAGATTAGATCGCGCCACTCCGCATATCCTGCCGGCACCGA

AGATGACGAAGGCATGGGCGAGGAACCGAGCCCGTTCCGTGGCCGTAGC

CGTGCTGCACCGCCGAATCTGTGGGCCGCACAGCGTTATGGTCGCGAGT

TGCGTCGCATGTCCGACGAGTTTGTTGACTCCTTCAAGAAAGGTTTACC

-continued

```
GCGTCCGAAATCTGCCGGTACCGCGACGCAGATGCGTCAGAGCAGCAGC
TGGACCCGCGTGTTTCAATCTTGGTGGGATCGTAATCTGGGTCGTGGTA
GCAGCGCACCGAGCCAA (Bad);
```
and (SEQ ID NO: 10)
```
TCTCAGTCTAACCGCGAACTGGTGGTGGACTTCCTGTCTTATAAACTGA
GCCAGAAAGGCTACTCCTGGAGCCAGTTCAGCGACGTAGAGGAGAACCG
TACCGAAGCTCCTGAAGGCACCGAGAGCGAGATGGAAACCCCATCCGCG
ATTAACGGCAACCCGTCCTGGCACCTGGCTGATTCTCCGGCGGTAAACG
GCGCAACTGGTCATTCTAGCTCCCTGGATGCACGTGAAGTAATCCCGAT
GGCCGCGGTTAAACAGGCGCTGCGTGAAGCTGGTGACGAATTTGAGCTG
CGCTACCGCCGTGCATTTTCTGATCTGACCTCCCAGCTGCACATCACGC
CGGGTACCGCATACCAAAGCTTCGAACAGGTGGTTAACGAACTGTTTCG
TGACGGCGTCAACTGGGCCGCATCGTGGCCTTTTTCTCTTTCGGCGGT
GCCCTGTGCGTCGAATCTGTTGACAAAGAAATGCAGGTTCTGGTGAGCC
GTATTGCGGCTTGGATGGCAACTTATCTGAACGATCACCTGGAACCGTG
GATCCAGGAAAACGGTGGTTGGGATACCTTCGTTGAACTGTACGGTAAC
AATGCTGCGGCGGAATCCCGTAAGGGTCAAGAACGTTTCAATCGCTGGT
TCCTGACCGGCATGACTGTTGCTGGTGTAGTTCTGCTGGGTTCTCTGTT
CTCCCGTAAA (B[[x]]clxL).
```

IL-2/Bcl-2 Family Fusion Proteins

"Fusion proteins" according to the present disclosure include IL-2 proteins joined to a Bcl-2 family member, with optional additional sequences or moieties (such as linkers), as described herein, as well as nucleic acid molecules encoding such fusion proteins. Also encompassed are recombinant nucleic acid molecules in which a nucleic acid sequence encoding a fusion protein is operably linked to a promoter, vectors containing such a molecule, and transgenic cells comprising such a molecule.

IL-2 (including cpIL-2 and IL-2 fragments and variants) can be linked to Bcl-2 family proteins, such as pro-apoptotic Bcl-2 family polypeptides comprising a BH3 domain as exemplified by Bad, Bik/Nbk, Bid, Bim/Bod, Hrk, Bak or Bax, or combinations thereof, or anti-apoptotic Bcl-2 family polypeptides as exemplified by Bcl-2, Bcl-$x_L$ or Bcl-w, as long as the combination retains either anti-apoptotic or pro-apoptotic activity, as desired. Any form or derivative of IL-2 can be used. For example, IL-2 or fragments of IL-2 that bind to the IL-2 receptor can be used. Additionally, multiple Bcl-2 family proteins or fragments or variants thereof, can be joined to IL-2 or fragments or variants thereof, or multiple IL-2 proteins or fragments or variants thereof, can be joined to Bcl-2 family proteins or fragments or variants thereof.

A cpIL-2, can be linked to a Bcl-2 family protein, such as pro-apoptotic Bcl-2 family polypeptides, such as those comprising a BH3 domain as exemplified by Bad, Bik/Nbk, Bid, Bim/Bod, Hrk, Bak or Bax or combinations thereof, or fragments or variants thereof, or anti-apoptotic Bcl-2 family polypeptides as exemplified by Bcl-2, Bcl-$x_L$ or Bcl-w, as long as the combination retains either anti-apoptotic or pro-apoptotic activity, as desired. Any form or derivative of cpIL-2 can be used. Additionally, multiple cpIL-2 proteins or fragments or variants thereof, can be joined to a Bcl-2 family protein or fragment or variants thereof, or multiple Bcl-2 family proteins or fragments or variants thereof, can be joined to cpIL-2 proteins or fragments or variants thereof.

Exemplary fusion proteins are listed in Table 1.

TABLE 1

IL-2/Bcl-2 Family Fusion Proteins

| Name | IL-2 | Linker | Bcl-2 Family Protein | Description |
|---|---|---|---|---|
| proS2 | PTSSSTKKTQLQLEHL LLCDLQMILNGINNYKN PKLTRMLTAKFYMPK KATELKHLQCLEEELK PLEEVLNLAHSKNFHF DPRDVVSNINVFVLEL KGSETTFMCEYADET ATIVEFLNRWITFSQSI ISTLT (SEQ ID NO: 3) | None | None | |
| proS2-BclxL | PTSSSTKKTQLQLEH LLLDLQMILNGINNYK NPKLTRMLTAKFYMP KKATELKHLQCLEEE LKPLEEVLNLAHSKNF HF DPRDVVSNINVFV LELKGSETTFMCEYA DETATIVEFLNRWITF SQSIISTLT (SEQ ID NO: 3) | GS | SQSNRELVVDFLS YKLSQKGYSWSQF SDVEENRTEAPEG TESEMETPSAING NPSWHLADSPAVN GATGHSSSLDARE VIPMAAVKQALREA GDEFELRYRRAFS DLTSQLHITPGTAY QSFEVVVNELFRD GVNWGRIVAFFSF GGALCVESVDKEM QVLVSRIAAWMAT YLNDHLEPWIQEN GGWDTFVELYGN NAAAESRKGQERF NRWFLTGMTVAGV VLLGSLFSRK (SEQ ID NO: 7) | |

TABLE 1-continued

IL-2/Bcl-2 Family Fusion Proteins

| Name | IL-2 | Linker | Bcl-2 Family Protein | Description |
|------|------|--------|----------------------|-------------|

Fusion Sequence:
PTSSSTKKTQLQLEHLLLDLQMILNGINNYKNPKLTRMLTAKFYMPKKATELKHLQCL
EEELKPLEEVLNLAHSKNFHFDPRDVVSNINVFVLELKGSETTFMCEYADETATIVEFL
NRWITFSQSIISTLTGSSQSNRELVVDFLSYFLSQKGYSWSQFSDVEENRTEAPEGTESE
METPSAINGNPSWHLADSPAVNGATGHSSSLDAREVIPMAAVKQALREAGDEFELRY
RRAFSDLTSQLHITPGTAYQSFEQVVNELFRDGVNWGRIAFFSFGGALCVESVDKEMQ
VLVSRIAAWMATYLNDHLEPWIQENGGWDTFVELYGNNAAAESRKGQERFNRWFLT
GMTVAGVVLLGSLFSRE (SEQ ID NO: 11)

| Name | IL-2 | Linker | Bcl-2 Family Protein | Description |
|------|------|--------|----------------------|-------------|
| cpproS2-BclxL | MLTAKFYMPKKATEL KHLQCLEEELKPLEE VLNLAHSKNFHFDPR DVVSNINVFVLELKGS ETTFMCEYADETATIV EFLNRWITFSQSIISTL T*GGNGG*PTSSSTKKT QLQLEHLLLDLQMILN GINNYKNPKLT (SEQ ID NO: 4) | GS | SQSNRELVVDFL SYKLSQKGYSW SQFSDVEENRTE APEGTESEMETP SAINGNPSWHLA DSPAVNGATGHS SSLDAREVIPMA AVKQALREAGDE FELRYRRAFSDL TSQLHITPGTAY QSFEQVVNELFR DGVNWGRIVAFF SFGGALCVESVD KEMQVLVSRIAA WMATYLNOHLEP WIQENGGWDTF VELYGNNAAAES RKGQERFNRWF LTGMTVAGVVLL GSLFSRK (SEQ ID NO: 7) | Circularly permuted version of proS2 linked to BclxL |

Fusion Sequence:
MLTAKFYMPKKATELKHLQCLEEELKPLEEVLNLAHSKNFHFDPRDVVSNINVFVLEL
KGSETTFMCEYADETATIVEFLNRWITFSQSIISTLT*GGNGG*PTSSSTKKTQLQLEHLLLD
LQMILNGINNYKNPKLTGSSQSNRELVVDFLSYKLSQKGYSWSQFSDVEENRTEAPEGT
ESEMETPSAINGNPSWHLADSPAVNGATGHSSSLDAREVIPMAAVKQALREAGDEFELR
YRRAFSDLTSQLHITPGTAYQSFEQVVNELFRDGVNWGRIVAFFSFGGALCVESVDKEM
QVLVSRIAAWMATYLNOHLEPWIQENGGWDTFVELYGNNAAAESRKGQERFNRWFLT
GMT VAGVVLLGSLFSRK (SEQ ID NO: 12)

| Name | IL-2 | Linker | Bcl-2 Family Protein | Description |
|------|------|--------|----------------------|-------------|
| proS2-Bad | PTSSSTKKTQLQLEH LLLCDLQMILNGINNYK NPKLTRMLTAKFYMP KKATELKHLQCLEEE LKPLEEVLNLAHSKNF HFDPRDVVSNINVFV LELKGSETTFMCEYA DETATIVEFLNRWITF SQSIISTLT (SEQ ID NO: 3) | GS | FQIPEFEPSEQ EDSSSAERGL GPSPAGDGPS GSGKHHRQAP GLLWDASHQQ EQPTSSSHHG GAGAVEIRSRH SAYPAGTEDD EGMGEEPSPF RGRSRAAPPN LWAAQRYGRE LRRMSDEFVD SFKKGLPRPKS AGTATQMRQS SSWTRVFQSW WDRNLGRGSS APSQ (SEQ ID NO: 8) | |

Fusion Sequence:
PTSSSTKKTQLQLEHLLLDLQMILNGINNYKNPKLTRMLTAKFYMPKKATELKHLQCL
EEELKPLEEVLNLAHSKNFHFDPRDVVSNINVFVLELKGSETTFMCEYADETATIVEFL
NRWITFSQSIISTLTGSFQIPEFEPSEQEDSSSAERGLGPSPAGDGPSGSGKHHRQAPGLL
WDASHQQEQPTSSSHHGGAGAVEIRSRHSAYPAGTEDDEGMGEEPSPFRGRSRAAPPN
LWAAQRYGRELRRMSDEFVDSFKKGLPRPKSAGTATQMRQSSSWTRVFQSWWDRNL
GRGSSAPSQ (SEQ ID NO: 13)

| Name | IL-2 | Linker | Bcl-2 Family Protein | Description |
|------|------|--------|----------------------|-------------|
| cpproS2-Bad | MLTAKFYMPKKATEL KHLQCLEEELKPLEE VLNLAHSKNFHFDPR DVVSNINVFVLELKGS ETTFMCEYADETATIV EFLNRWITFSQSIISTL TGGNGGPTSSSTKKT | GS | FQIPEFEPSEQ EDSSSAERGL GPSPAGDGPS GSGKHHRQAP GLLWDASHQQ EQPTSSSHHG GAGAVEIRSRH | Circularly permuted version of proS2 linked to Bad |

TABLE 1-continued

IL-2/Bcl-2 Family Fusion Proteins

| Name | IL-2 | Linker | Bcl-2 Family Protein | Description |
|---|---|---|---|---|
| | QLQLEHLLLDLQMILN<br>GINNYKNPKLT<br>(SEQ ID NO: 4) | | S<u>A</u>YPAGTEDD<br>EGMGEEPSPF<br>RGRSR<u>A</u>APPN<br>LWAAQRYGRE<br>LRRMSDEFVD<br>SFKKGLPRPKS<br>AGTATQMRQS<br>SSWTRVFQSW<br>WDRNLGRGSS<br>APSQ<br>(SEQ ID NO: 8) | |

Fusion Sequence:
MLT<u>A</u>KFYMPKKATELKHLQCLEEELKPLEEVLNLA<u>H</u>SKNFH<u>FD</u>PRD<u>VV</u>SNINV<u>F</u>VLEL
KGSETTFMCEYADETATIVEFLNRWITF<u>S</u>QSIISTLTGGNGGPTSSSTKKTQLQLEHLLLD
LQMILNGINNYKNPKLTGSFQIPEFEPSEQEDSSSAERGLGPSPAGDGPSGSGKHHRQAP
GLLWDASHQQEQPTSSSHHGGAGAVEIRSRHS<u>A</u>YPAGTEDDEGMGEEPSPFRGRSR<u>A</u>A
PPNLWAAQRYGRELRRMSDEFVDSFKKGLPRPKSAGTATQMRQSSSWTRVFQSWWD
RNLGRGSSAPSQ (SEQ ID NO: 14)

The joining or "fusion" of an IL-2 protein to a Bcl-2 family member may be direct, such that one portion of the IL-2 protein is directly attached to a portion of the Bcl-2 family member. For example, one end of the amino acid sequence of a IL-2 protein can be directly attached to an end of the amino acid sequence of the Bcl-2 family member. For example, the C-terminus of the IL-2 protein can be linked to the N-terminus of the Bcl-2 family member, or the C-terminus of the Bcl-2 family member can be linked to the N-terminus of the IL-2 protein. Methods of generating such fusion proteins are routine in the art, for example using recombinant molecular biology methods.

Linkers

In some embodiments, an IL-2 protein moiety can be linked to the Bcl-2 family member moiety indirectly through a linker. The linker can serve, for example, simply as a convenient way to link the two moieties, as a means to spatially separate the two moieties, to provide an additional functionality to the IL-2 protein or the Bcl-2 family member, or a combination thereof.

In general, the linker joining the IL-2 protein moiety and the Bcl-2 family member moiety can be designed to (1) allow the two molecules to fold and act independently of each other, (2) not have a propensity for developing an ordered secondary structure which could interfere with the functional domains of the two moieties, (3) have minimal hydrophobic or charged characteristics which could interact with the functional protein domains and/or (4) provide steric separation of the two regions. For example, in some instances, it may be desirable to spatially separate the IL-2 protein and the Bcl-2 family member to prevent the IL-2 protein from interfering with the activity of the Bcl-2 family member and/or the Bcl-2 family member interfering with the activity of the IL-2 protein. The linker can also be used to provide, for example, lability to the connection between the IL-2 protein and the Bcl-2 family member, an enzyme cleavage site (for example, a cleavage site for a protease), a stability sequence, a molecular tag, a detectable label, or various combinations thereof. In some embodiments, a linker can be present between two domains of an IL-2 (such as in a cp molecule) or Bcl-2 family member.

The linker can be bifunctional or polyfunctional, i.e., contain at least about a first reactive functionality at, or proximal to, a first end of the linker that is capable of bonding to, or being modified to bond to, the IL-2 protein and a second reactive functionality at, or proximal to, the opposite end of the linker that is capable of bonding to, or being modified to bond to, the Bcl-2 family member being modified. The two or more reactive functionalities can be the same (i.e. the linker is homobifunctional) or they can be different (i.e. the linker is heterobifunctional).

The length and composition of a linker can be varied considerably. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the activity of the IL-2 protein and/or Bcl-2 family member.

Linkers suitable for use in a fusion protein according to the present disclosure include peptides. The linker can be attached to the IL-2 moiety and/or the Bcl-2 family member moiety using recombinant DNA technology. Such methods are well-known in the art and details of this technology can be found, for example, in Sambrook, et al. Molecular Cloning: A Laboratory Manual $2^{nd}$ ed., Cold Spring Harbor Laboratory, Cold Spring Harbor Laboratory Press, Cold Spring Harbor, N.Y., 1980 or Ausubel et al. Current Protocols in Molecular Biology, John Wiley & Sons, 1994) or updates thereto.

The linked peptides can have a chain length of 1 to 500 amino acid residues (such as 1 to 100, 1 to 50, 6 to 30, 1 to 40, 1 to 20, or less than 30 amino acids or 5 to 10 amino acids). In some embodiments, a linker can be 2, 3, 4, 5, 6, 7, or 8 amino acids in length, or can be about 10, 20, 30, 40 or 50 amino acids in length.

Typically, surface amino acids in flexible protein regions include Gly, Asn and Ser, and such amino acids can be used in linker sequences. Other neutral amino acids, such as Thr and Ala, can also be used in the linker sequence. Additional amino acids can be included in the linker to provide unique restriction sites in the linker sequence to facilitate construction of the fusions. In some embodiments, a linker may for instance include the amino acid sequence Gly-Ser (GS) or may be the amino acid sequence Gly-Ser (GS) or may include a ubiquitin sequence:

(SEQ ID NO: 15)
GGGSMQIFVRTLTGRTITLEVEPSDTIENVRARIQDREGIPPDQQRLIFAG
RQLEDGRTLSDYNIQRESTLHLVLRLRGGGS or variant thereof. Ubiquitin molecules suitable for use as linkers are described in, for example, Bachran, C. et al. "Anthrax toxin-mediated delivery of the *Pseudomonas* exotoxin A enzymatic domain to the cytosol of tumor cells via cleavable ubiquitin fusions MBio. 2013 April 30;4(3): e00201-13, or in PCT publication WO/2012/139112.

Peptide linkers that are susceptible to cleavage by enzymes of the complement system, urokinase, tissue plasminogen activator, trypsin, plasmin, or another enzyme having proteolytic activity may be used in one example. According to another example, the IL-2 protein can be attached via a linker susceptible to cleavage by enzymes having a proteolytic activity such as a urokinase, a tissue plasminogen activator, plasmin, thrombin or trypsin. In addition, the IL-2 protein can be attached to the Bcl-2 family member via disulfide bonds (for example, the disulfide bonds on a cysteine molecule). For example, in the context of pro-apoptotic Bcl-2 family proteins, since many tumors naturally release high levels of glutathione (a reducing agent) this can reduce the disulfide bonds with subsequent release of the pro-apoptotic Bcl-2 family member at the site of delivery.

In some embodiments, a fusion protein according to the present disclosure may include a Bcl-2 family member and an IL-2 protein linked by a cleavable linker region. In another embodiment, the cleavable linker region can be a protease-cleavable linker, although other linkers, cleavable for example by small molecules, may be used. Examples of protease cleavage sites include those cleaved by factor Xa, thrombin and collagenase. In one example, the protease cleavage site include those cleaved by a protease that is associated with a disease. In another example, the protease cleavage site is one that is cleaved by a protease that is up-regulated or associated with cancers in general. Examples of such proteases are uPA, the matrix metalloproteinase (MMP) family, the caspases, elastase, prostate specific antigen (PSA, a serine protease), and the plasminogen activator family, as well as fibroblast activation protein. In still another example, the cleavage site is cleaved by a protease secreted by cancer-associated cells. Examples of these proteases include matrixmetalloproteases, elastase, plasmin, thrombin, and uPA. In another example, the protease cleavage site is one that is up-regulated or associated with a specific cancer. The precise sequences are available in the art and the skilled person will have no difficulty in selecting a suitable cleavage site. By way of example, the protease cleavage region targeted by Factor Xa is IEGR (SEQ ID NO: 18). The protease cleavage region targeted by enterokinase is DDDDK (SEQ ID NO: 19). The protease cleavage region targeted by thrombin is LVPRG (SEQ ID NO: 20). In one example, the cleavable linker region is one which is targeted by endocellular proteases.

The linker can be attached to the IL-2 protein moiety and/or Bcl-2 family member moiety using routine techniques as known in the art.

Preparation of IL-2/Bcl-2 Family Fusion Proteins

Fusion proteins can be prepared using routine methods as known in the art. Fusion proteins, as well as modifications thereto, can be made, for example, by engineering the nucleic acid encoding the fusion protein using recombinant DNA technology or by peptide synthesis. Modifications to the fusion protein may be made, for example, by modifying the fusion protein polypeptide itself, using chemical modifications and/or limited proteolysis. Combinations of these methods may also be used to prepare the fusion proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the fusion proteins can be produced in a prokaryotic host (e.g., *E. coli*, *A. salmonicida* or *B. subtilis*) or in a eukaryotic host (e.g., *Saccharomyces* or *Pichia*, mammalian cells, e.g., COS, NIH 3T3, CHO, BHK, 293, or HeLa cells; or insect cells (baculovirus)). The fusion proteins can be purified from the host cells using standard techniques known in the art.

Sequences for various exemplary fusion proteins are provided in Table 1. Variants and homologs of these sequences can be cloned, if an alternative sequence is desired, using standard techniques (see, for example, Ausubel et al., Current Protocols in Molecular Biology, Wiley & Sons, NY (1997 and updates); Sambrook et al., Sambrook, et al. Molecular Cloning; A Laboratory Manual, $2^{nd}$ ed., Cold Spring Harbor Laboratory, Cold Spring Harbor Laboratory Press, Cold Spring Harbor, N.Y., 1989 or updates thereto). For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding either the IL-2 moiety or the Bcl-2 family moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the fusion protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered fusion protein can be used to produce the fusion protein.

The expression vector may additionally contain heterologous nucleic acid sequences that facilitate the purification of the expressed fusion protein, such as affinity tags such (e.g., metal-affinity tags, histidine tags, avidin/streptavidin encoding sequences, glutathione-S-transferase (GST) encoding sequences, maltose binding protein (MBP) encoding sequences or biotin encoding sequences). In one example, such tags are attached to the N- or C-terminus of a fusion protein, or can be located within the fusion protein. The tags can be removed from the expressed fusion protein prior to use according to methods known in the art. Alternatively, the tags can be retained on the fusion protein, providing that they do not interfere with the ability of the desired activity of the fusion protein.

The fusion protein can include one or more linkers, as well as other moieties, as desired and/or as discussed herein. These can include a binding region, such as avidin or an epitope, or a tag such as a polyhistidine tag, which can be useful for purification and processing of the fusion protein, as well as other linkers as described herein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a fusion protein. Such variations in the DNA sequence encoding a fusion protein can be used to optimize for codon preference in a host cell used to express the protein, or may contain other sequence changes that facilitate expression.

A covalent linkage of a IL-2 protein directly to a Bcl-2 family member or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Assays

Fusion proteins can be assayed using standard techniques known in the art or described herein.

For example, the ability of the fusion proteins to kill or inhibit growth of cells can be assayed in vitro using suitable cells, typically a cell line expressing the target or a cancer cell. In general, cells of the selected test cell line are grown to an appropriate density and the candidate fusion protein is added. The fusion protein can be added to the culture at around at least 1 ng/mL, at least 1 ug/mL, or at least 1 mg/mL, such as from about 0.01 ug/mL to about 1 mg/mL, from about 0.10 ug/mL to about 0.5 mg/mL, from about 1 ug/mL to about 0.4 mg/mL. In some examples, serial dilutions are tested. After an appropriate incubation time (for example, about 48 to 72 hours), cell survival or growth is assessed. Methods of determining cell survival are well known in the art and include, but are not limited to, the resazurin reduction test (see Fields & Lancaster Am. Biotechnol. Lab., 11:48-50, 1993, O'Brien et al., Eur. J. Biochem., 267:5421-5426, 2000 or U.S. Pat. No. 5,501, 959), the sulforhodamine assay (Rubinstein et al., J. Natl. Cancer Inst., 82:113-118, 1999) or the neutral red dye test (Kitano et al., Euro. J. Clin. Investg., 21 53-58, 1991, West et al., J. Investigative Derm., 99:95-100, 1992) or trypan blue assay. Numerous commercially available kits may also be used, for example the CellTiter 96®AQueous One Solution Cell Proliferation Assay (Promega). Cytotoxicity is determined by comparison of cell survival in the treated culture with cell survival in one or more control cultures, for example, untreated cultures and/or cultures pre-treated with a control compound (typically a known therapeutic), or other appropriate control.

Additional assays are described in, for example, Crouch et. al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1:611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Fusion proteins that confer selectivity for a specific type of cancer may be tested for their ability to target that specific cancer cell type. For example, a fusion protein comprising a specific IL-2 that targets cells displaying IL-2Rβ or IL-2Rγ can be assessed for its ability to selectively target such cells by comparing the ability of the fusion protein to kill cancer cells to its ability to kill a normal cell, or a different type of cancer cell (e.g., one that does not express the targeted IL-2R). Alternatively, flow cytometric methods, as are known in the art, may be used to determine if a fusion protein comprising a IL-2Rβ or IL-2Rγ chain-specific IL-2 is able to selectively target a specific type of cell. Binding of a labeled antibody to the bound fusion protein will indicate binding of the fusion protein to the target. In some embodiments, fusion proteins according to the invention may be used to increase or decrease the population of immune cells, such as natural killer cells or regulatory T cells.

Similarly, assays for measuring cell apoptosis are known in the art. Apoptotic cells are characterized by characteristic morphological changes, including chromatin condensation, cell shrinkage and membrane blobbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

A variety of cell lines suitable for testing the candidate fusion proteins are known in the art and many are commercially available (for example, from the American Type Culture Collection, Manassas, Va.). Similarly, animal models are known in the art and many are commercially available.

Therapeutic Indications and Uses

The fusion proteins including an IL-2 protein and a Bcl-2 family member, as described herein, can be used for a variety of therapeutic purposes. In general, the fusion proteins described herein can be used in the treatment or prophylaxis of any disease, disorder or condition which involves cells which express an IL-2R, and which would be benefited by: inhibiting cell proliferation or enhancing cell death, or enhancing cell proliferation or inhibiting cell death. In some embodiments, the fusion proteins described herein can be used in the treatment or prophylaxis of any disease, disorder or condition which involves cells which express a IL-2Rβ or IL-2Rγ and in which selection of one type of receptor over the other is useful, and would either be benefited by inhibiting cell proliferation or enhancing cell death, or be benefited by enhancing cell proliferation or inhibiting cell death and which In some embodiments, the fusion proteins described herein can be used in the treatment or prophylaxis of cancers or autoimmune diseases.

In some embodiments, a fusion protein including a pro-apoptotic Bcl-2 family member can be used to induce apoptosis or cell death or to treat a disorder associated with abnormal apoptosis or cell proliferation, such as cancer. As used herein, the terms "cancel," "cancerous," "hyperproliferative," or "neoplastic" refer to cells having the capacity for autonomous growth (e.g., an abnormal state or condition characterized by rapidly proliferating cell growth). Hyperproliferative and neoplastic disease states may be categorized as pathologic (e.g., as a deviation from normal but not associated with a disease state). Accordingly, by a "cancer" or "neoplasm" is meant any unwarned growth of cells serving no physiological function. In general, a cell of a neoplasm has been released from its normal cell division control, i.e., a cell whose growth is not regulated by the ordinary biochemical and physical influences in the cellular environment. In most cases, a neoplastic cell proliferates to form a clone of cells which are either benign or malignant. Examples of cancers or neoplasms include, without limitation, transformed and immortalized cells, tumours, and carcinomas such as breast cell carcinomas and prostate carcinomas. The term cancer includes cell growths that are technically benign but which carry the risk of becoming malignant. By "malignancy" is meant an abnormal growth of any cell type or tissue. The term malignancy includes cell growths that are technically benign but which carry the risk of becoming malignant. This term also includes any cancer, carcinoma, neoplasm, neoplasia, or tumor. The terms are therefore meant to include all types of cancerous growths or oncogenic processes, metastatic tissue or malignantly transformed cells, tissues or organs, irrespective of histopathologic type or stage of invasiveness. In some embodiments, a fusion protein including a pro-apoptotic Bcl-2 family member is not used in connection with a cancer affecting a stem cell.

Most cancers fall within three broad histological classifications: carcinomas, which are the predominant cancers and are cancers of epithelial cells or cells covering the external or internal surfaces of organs, glands, or other body structures (e.g., skin, uterus, lung, breast, prostate, stomach, bowel), and which tend to mestastasize; sarcomas, which are derived from connective or supportive tissue (e.g., bone, cartilage, tendons, ligaments, fat, muscle); and hematologic tumors, which are derived from bone marrow and lymphatic tissue. Examples of cancers include, without limitation, carcinomas, sarcomas, and hematopoietic neoplastic disorders e.g., leukemia.

Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body).

Sarcomas may be osteosarcomas or osteogenic sarcomas (bone), chondrosarcomas (cartilage), leiomyosarcomas (smooth muscle), rhabdomyosarcomas (skeletal muscle), mesothehal sarcomas or mesotheliomas (membranous lining of body cavities), fibrosarcomas (fibrous tissue), angiosarcomas or hemangioendotheliomas (blood vessels), liposareomas (adipose tissue), gliomas or astrocytomas (neurogenic connective tissue found in the brain), myxosarcomas (primitive embryonic connective tissue), or mesenchymous or mixed mesodermal tumors (mixed connective tissue types).

Hematopoietic neoplastic disorders include diseases involving hyperplastic/neoplastic cells of hematopoietic origin e.g., arising from myeloid, lymphoid or erythroid lineages or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myeloenous leukemia (AML) and chronic myeloenous leukemia (CML); lymphoid malignancies include but are not limited to acute lymphoblastic leukemia (ALL), which includes B-lineage ALL and T-lineage ALL, chronic lymphocytic leukemia (CLL), prolymphocytic leukemia (PLL), hairy cell leukemia, and Waldenstrom's macroglobulinemia.

Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (IGF), Hodgkin's disease and Reed-Stemberg diseases.

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body, that is different from the primary site. Cancers named based on primary site may be correlated with histological classifications. For example, lung cancers are generally small cell lung cancers or non-small cell lung cancers, which may be squamous cell carcinoma, adenocarcinoma, or large cell carcinoma, skin cancers are generally basal cell cancers, squamous cell cancers, or melanomas. Lymphomas may arise in the lymph nodes associated with the head, neck and chest, as well as in the abdominal lymph nodes or in the axillary or inguinal lymph nodes. Identification and classification of types and stages of cancers may be performed by using for example information provided by the Surveillance, Epidemiology, and End Results (SEER) Program of the National Cancer Institute.

The fusion proteins can be used to treat, stabilize or prevent cancer. Fusion proteins can also be used in the treatment of indolent cancers, recurrent cancers including locally recurrent, distantly recurrent and/or refractory cancers (i.e. cancers that have not responded to other anti-cancer treatments), metastatic cancers, locally advanced cancers and aggressive cancers. In these contexts, the fusion proteins may exert either a cytotoxic or cytostatic effect resulting in, for example, a reduction in the number or growth of cancer cells, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptoms associated with a tumor, or an increase in the overall survival time of a subject having cancer.

Other examples of proliferative and/or differentiative disorders that can be treated using a fusion protein including a pro-apoptotic Bcl-2 family member include skin disorders, inflammatory disorders, etc.

The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

Patients amenable to treatment may also have psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

In some embodiments, a fusion protein including a pro-apoptotic Bcl-2 family protein member, or a fragment thereof, can be used in treating autoimmune diseases, rheumatoid arthritis, Crohn's disease, psoriasis, inflammatory bowel disease, insulitis, Type 1 diabetes, multiple sclerosis, vasculitis, scleroderma, sytemic lupus erythematosus, graft versus host disease (GVHD), HIV infection, uveitis, systemic mastocytosis, leishmaniasis, etc.

In some embodiments, a fusion protein including a pro-apoptotic Bcl-2 family protein member, or a fragment thereof, can be used in treating a cancer, such as leukemias and lymphomas, cutaneous T cell lymphoma, hairy cell leukemia, metastatic renal cell carcinoma, fallopian tube cancer, melanoma, chronic lymphocytic leukemia, non-Hodgkins lymphoma, follicular lymphoma, ovarian cancer, peritoneal carcinoma, etc.

In some embodiments, fusion proteins according to the invention may be used to increase or decrease the population of immune cells, such as natural killer cells or regulatory T cells.

In some embodiments, a fusion protein including a pro-apoptotic Bcl-2 family protein member and an IL-2 variant that exhibits enhanced binding to, and is therefore selective for, IL-2Rβ (such as ProS2-Bad, as described herein, or a version lacking the F42A mutation), or a fragment thereof, can be used to inhibit the survival or proliferation or to enhance the death or apoptosis of natural killer (NK) cells, thus depleting the number of NK cells. In some embodiments, such a fusion protein will not substantially alter the survival, proliferation, death or apoptosis of a regulatory T cell. In some embodiments, a fusion protein including a pro-apoptotic Bcl-2 family protein member (such as ProS2-Bad, as described herein, or a version lacking the F42A mutation), or a fragment thereof, can be used to treat an autoimmune disease.

In some embodiments, a fusion protein including a pro-apoptotic Bcl-2 family protein member and an IL-2 variant that disrupts the association between IL-2Rβ and IL-2Rγ, or a fragment thereof, can be used to inhibit the survival or proliferation or to enhance the death or apoptosis of regulatory T cells. In some embodiments, such a fusion protein will not substantially alter the survival, proliferation, death or apoptosis of a NK cell. In some embodiments, a fusion protein including a pro-apoptotic Bcl-2 family protein member and an IL-2 variant that disrupts the association between IL-2Rβ and IL-2Rγ, or a fragment thereof, can be used to treat a cancer, such as a cancer that involves a cell expressing IL-2Rα.

In some embodiments, a fusion protein including a pro-apoptotic Bcl-2 family protein member, or a fragment thereof, is capable of inhibiting cell survival, inhibiting cell proliferation, or enhancing cell death or apoptosis. In some embodiments, the IL-2-pro-apoptotic Bcl-2 family fusion protein is capable of inhibiting cell survival, inhibiting cell proliferation, or enhancing cell death or apoptosis, when compared to a suitable control, such as IL-2 alone, IL-2 joined to a non-pro-apoptotic Bcl-2 family protein, etc. A suitable control may also include a previously-established standard. Accordingly, any test or assay for determining the activity or efficacy of an IL-2-pro-apoptotic Bcl-2 family fusion protein may be compared to the established standard and it may not be necessary to include a control for comparison each time. By "inhibiting cell survival" is meant decreasing (e.g., by at least 10%, 20%, 30%, or by as much as 50%, 75%, 85% or 90% or more) the probability that a cell at risk of cell death will survive. By "inhibiting cell proliferation" is meant decreasing (e.g., by at least 10%, 20%, 30%, or by as much as 50%, 75%, 85% or 90% or more) the growth or proliferation of a cell. By "enhancing cell death or apoptosis" is meant increasing (e.g., by at least 10%, 20%, 30%, or by as much as 50%, 75%, 85% or 90% or more) the probability that a cell at risk of cell death will undergo apoptotic, necrotic, or any other form of cell death.

In some embodiments, a fusion protein including a pro-apoptotic Bcl-2 family protein member, or a fragment thereof, is capable of inhibiting cell survival, inhibiting cell proliferation, or enhancing cell death or apoptosis by at least 20%, 30%, or by as much as 50%, 75%, 85% or 90% or more, when compared to a cell cultured under similar conditions but not contacted with the fusion protein. Suitable assays for measuring the inhibition of cell survival, inhibition of cell proliferation, or enhancement of cell death or apoptosis are described herein or known in the art.

In some embodiments, the $IC_{50}$ of a fusion protein including a pro-apoptotic Bcl-2 family protein member, or a fragment thereof, in inhibiting cell survival, inhibiting cell proliferation, or enhancing cell death or apoptosis, can be in the range from about 0.1 ng/mL to about 10,000 ng/mL, or any value therebetween, such as about 0.5 ng/mL, 1 ng/mL, 5 ng/mL, 10 ng/mL, 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, or 1000 ng/mL.

In alternative embodiments, a fusion protein including an anti-apoptotic Bcl-2 family member can be used to enhance cell proliferation or treat a disease, disorder or condition associated with cell death or apoptosis, such as hypoxia, ischemia, reperfusion, autoimmune diseases, reactive arthritis, rheumatoid arthritis, Sjogren syndrome, systemic lupus erythematosus, Type 1 diabetes, etc.), receipt of a cell, tissue or organ transplantation, cytotoxic drug treatment, receipt of chemotherapy, receipt of immunotherapy, or receipt of radiation therapy.

In some embodiments, a fusion protein including an anti-apoptotic Bcl-2 family member or a pro-apoptotic Bcl-2 family member can be used in treating myelodysplastic syndrome, alopecia, HIV infection, chronic hepatitis C, mycosis fungoides, Sezary syndrome, Type 1 diabetes, Wiskott Aldrich syndrome, X-linked thrombocytopenia, etc.

In some embodiments, a fusion protein including an anti-apoptotic Bcl-2 family member can be used in treating cancers, such as metastatic renal cell carcinoma, melanoma, CNS tumours (e.g., glioblastoma or neuroblastoma), liver cancer, bladder cancer, lung cancer, colorectal cancer, leukemias and lymphomas (e.g., acute myeloid leukemia; non-Hodgkins lymphoma or B-chronic lymphocytic leukemia), solid tumours, prostate cancer, head and neck cancer, breast cancer, sarcomas, pulmonary metastasis, gastric adenocarcinoma, etc.

In some embodiments, a fusion protein including an anti-apoptotic Bcl-2 family member or a pro-apoptotic Bcl-2 family member can be used as a vaccine adjuvant for cancer immunotherapy, in cellular adaptive immunotherapy for cancer, for ex vivo expansion of immune cells for cancer therapy, for ex vivo expansion and maturation of dendritic cells, or for in vivo or ex vivo immune modulation for the treatment of cancer or to propagate and expand engineered T cells for, for example, adoptive cell transfer therapy and chimeric antigen receptor (CAR) therapy (CAR-T). In some embodiments, a fusion protein including an anti-apoptotic Bcl-2 family member can be used in the expansion of natural killer (NK) cells. In some embodiments, a fusion protein including a pro-apoptotic Bcl-2 family member can be used to deplete or reduce the population of regulatory T cells.

In alternative embodiments, a fusion protein including an anti-apoptotic Bcl-2 family member can be used to stimulate dendritic cells or cell-based vaccines. In alternative embodiments, a fusion protein including an anti-apoptotic Bcl-2 family member can be used as vaccine adjuvants for example for cancer therapy or the treatment of infectious diseases. In alternative embodiments, a fusion protein including an anti-apoptotic Bcl-2 family member can be used to stimulate the immune system, for example, in the treatment of infectious diseases or transplantation.

In some embodiments, a fusion protein including an anti-apoptotic Bcl-2 family member and an IL-2 variant that exhibits enhanced binding to, and is therefore selective for, IL-2Rβ (such as ProS2-BclX$_L$ as described herein), or a fragment thereof, can be used to enhance the survival or proliferation or to inhibit the death or apoptosis of natural killer (NK) cells, thus increasing or stimulating the number of NK cells. In some embodiments, a fusion protein including an anti-apoptotic Bcl-2 family member and an IL-2 variant that exhibits enhanced binding to, and is therefore selective for, IL-2Rβ (such as ProS2-BclX$_L$ as described herein), or a fragment thereof, can be used to treat a cancer.

In some embodiments, a fusion protein including an anti-apoptotic Bcl-2 family protein, or fragment thereof, is capable of enhancing cell survival, enhancing cell proliferation, or inhibiting cell death or apoptosis. In some embodiments, the IL-2-anti-apoptotic Bcl-2 family fusion protein is capable of enhancing cell survival, enhancing cell proliferation, or inhibiting cell death or apoptosis, when compared to a suitable control, such as IL-2 alone, IL-2 joined to a non-anti-apoptotic Bcl-2 family protein, etc. A suitable control may also include a previously-established standard. Accordingly, any test or assay for determining the activity or efficacy of an IL-2-anti-apoptotic Bcl-2 family fusion protein may be compared to the established standard and it may not be necessary to include a control for comparison each time. By "enhancing cell survival" is meant increasing (e.g., by at least 10%, 20%, 30%, or by as much as 50%, 75%, 85% or 90% or more) the probability that a cell at risk of cell death will survive. By "enhancing cell proliferation" is meant increasing (e.g., by at least 10%, 20%, 30%, or by as much as 50%, 75%, 85% or 90% or more) the growth or proliferation of a cell. By "inhibiting cell death or apoptosis" is meant reducing (e.g., by at least 10%, 20%, 30%, or by as much as 50%, 75%, 85% or 90% or more) the probability that a cell at risk of cell death will undergo apoptotic, necrotic, or any other form of cell death.

In some embodiments, a fusion protein including an anti-apoptotic Bcl-2 family protein, or fragment thereof, is capable of enhancing cell survival, enhancing cell proliferation, or inhibiting cell death or apoptosis by at least 20%, 30%, or by as much as 50%, 75%, 85% or 90% or more, when compared to a cell cultured under similar conditions but not contacted with the fusion protein.

In some embodiments, a fusion protein including an anti-apoptotic Bcl-2 family protein, or fragment thereof, is capable of enhancing cell survival, enhancing cell proliferation, or inhibiting cell death or apoptosis by at least 20%, 30%, or by as much as 50%, 75%, 85% or 90% or more, compared to native IL-2, when administered at concentrations ranging from about 10 ng/mL to about 10,000 ng/mL, or any value therebetween, such as about 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1500 ng/mL, 2000 ng/mL, 2500 ng/mL, 3000 ng/mL, 3500 ng/mL, 4000 ng/mL, 4500 ng/mL, 5000 ng/mL, 5500 ng/mL, 6000 ng/mL, 6500 ng/mL, 7000 ng/mL, 7500 ng/mL, 8000 ng/mL, 8S00 ng/mL, 9000 ng/mL, 9500 ng/mL, or 10000 ng/mL.

Suitable assays for measuring the enhancement of cell survival, enhancement of cell proliferation, or inhibition of cell death or apoptosis are described herein or known in the art.

"Target cells" include, without limitation, neurons, lymphocytes, stem cells, epithelial cells, cancer cells, neoplasm cells, immune cells and others, including hyper-proliferative cells. The target cell chosen will depend on the disease or injury or condition the fusion protein is intended to treat Pharmaceutical Compositions, Dosages and Administration Pharmaceutical compositions according to the present disclosure can include one or more fusion proteins and one or more non-toxic, pharmaceutically-acceptable carriers, diluents, excipients and/or adjuvants. Such compositions can be suitable for use in treatment of therapeutic indications as described herein.

If desired, other active ingredients may be included in the compositions. Accordingly, in some embodiments, a fusion protein including a pro-apoptotic Bcl-2 family member can be administered in therapeutically-effective amounts together with one or more anti-cancer or other therapeutics. The fusion protein(s) can be administered before, during or after treatment with the anti-cancer or other therapeutic. An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosfamide, danorubicin, doxorubicin, epirubicin, mitoxantrone, vincristine, vinblastine, vinorelbine, etoposide, teniposide, paclitaxel, docetaxel, gemcitabine, cytosine, arabinoside, bleomycin, neocarcinostatin, suramin, taxol, mitomycin C, Avastin, Herceptin®, fluorouracil, temozolamide, etc. The fusion protein(s) are also suitable for use with standard combination therapies employing two or more chemotherapeutic agents. It is to be understood that anti-cancer therapeutics includes novel compounds or treatments developed in the future.

The fusion protein can also be administered in combination with a sensitizing agent, such as a radio-sensitizer (see for example Diehn et al., J. Natl. Cancer Inst. 98:1755-7, 2006). Generally a sensitizing agent is any agent that increases the activity of a fusion protein. For example, a sensitizing agent will increase the ability of a fusion protein to inhibit cancer cell growth or kill cancer cells. Exemplary sensitizing agents include antibodies to IL-10, bone morphogenic proteins and HDAC inhibitors (see for example Sakariassen et al., Neoplasia 9(11):882-92, 2007). These sensitizing agents can be administered before or during treatment with the fusion protein. Exemplary dosages of such sensitizing agents include at least 1 ug/mL, such as at least 10 ug/mL, at least 100 ug/mL, for example 5-100 ug-mL or 10-90 ug/mL. The sensitizing agents can be administered daily, three times a week, twice a week, once a week or once every two weeks. Sensitizing agent can also be administered after treatment with the fusion protein is finished.

The fusion proteins may be used as part of a neo-adjuvant therapy (to primary therapy), as part of an adjuvant therapy regimen, where the intention is to cure the cancer in a subject. The fusion proteins can also be administered at various stages in tumor development and progression, including in the treatment of advanced and/or aggressive neoplasias (e.g., oven disease in a subject that is not amenable to cure by local modalities of treatment, such as surgery or radiotherapy), metastatic disease, locally advanced disease and/or refractory tumors (e.g., a cancer or tumor that has not responded to treatment). "Primary therapy" refers to a first line of treatment upon the initial diagnosis of cancer in a subject. Exemplary primary therapies may involve surgery, a wide range of immunotherapies, chemotherapies and radiotherapy. "Adjuvant therapy" refers to a therapy that follows a primary therapy and that is administered to subjects at risk of relapsing. Adjuvant systemic therapy is begun soon alter primary therapy, for example 2, 3, 4, 5, or 6 weeks after the last primary therapy treatment to delay recurrence, prolong survival or cure a subject. As discussed herein, it is contemplated that the fusion proteins can be used alone or in combination with one or more other chemotherapeutic agents as part of an adjuvant therapy. Combinations of the fusion proteins and standard chemotherapeutics may act to improve the efficacy of the chemotherapeutic and, therefore, can be used to improve standard cancer therapies. This application can be particularly important in the treatment of drug-resistant cancers which are not responsive to standard treatment.

In cancer, the microenvironment of a tumor contains both malignant and non-malignant cells. The tumor microenvironment can be identified using one or more of the following criteria: (a) a region comprising non-malignant cells which share the same physiological environment, or which are directly adjacent to malignant cells; (b) the extended tumor region; (c) an area of inflammation surrounding or proximal to a tumor; (d) an area in which the number or rate of proliferation of regulatory T cells is elevated; and (e) an area in which macrophages, dendritic cells, or myeloid-derived suppressor cells are elevated. Within the context of non-solid tumor types, the tumor microenvironment may also be determined by the local cell-cell interactions between malignant cells and between malignant cells and any adjacent or nearby non-malignant cells. Such interactions may include, for example, cell adhesion events and/or paracrine effects of soluble mediators produced by one cell (malignant or non-malignant) on another cell (malignant or non-malignant) in the tumor microenvironment.

The non-malignant cells in the tumor microenvironment can be important for tumor initiation and progression (Reynolds et al., Cancer Res., 1996, 56(24):5754-5757). The non-malignant cells, also called stromal cells, occupy or accumulate in the same cellular space as malignant cells, or the cellular space adjacent or proximal to malignant cells, which modulate tumor cell growth or survival. For example, non-malignant cells that normally function to support inflammatory and immune response can be capable of contributing to tumor initiation or progression. Accordingly, in alternative embodiments, a fusion protein including a pro-apoptotic Bcl-2 family member can be used for inhibiting cell survival, inhibiting cell proliferation, or enhancing cell death or apoptosis of a non-malignant cell that expresses an IL-2R in a tumour microenvironment. Such non-malignant cells can be immunoregulatory or inflammatory cells such as antigen presenting cells (e.g., macrophages, dendritic cells, B cells) or myeloid-derived suppressor cells (e.g., myeloid-derived monocytes and tie-2-expressing monocytes) present within the tumor microenvironment, and inhibition of T cell subsets that function to support tumor progression (e.g., regulatory T cells and Th2 helper cells) and/or suppressing production of one or more inflammatory cytokines in a tumor microenvironment. Among the non-malignant cells of a tumor microenvironment are regulatory T cells, which are observed in higher frequencies in a number of tumors, including Hodgkin's lymphoma, non-Hodgkin's lymphoma (Shi et al., Ai Zheng., 2004, 23(5):

597-601 (abstract only)), malignant melanoma (Viguier et al., J. Immunol., 2004, 173(2):1444-53; Javia et al., J. Immunother., 2003, 26(1):85-93), and cancers of the ovary (Woo et al., Cancer Res., 2001, 61(12):4766-72), gastrointestinal tract (Ichihara et al., Clin Cancer Res., 2003, 9(12): 4404-4408; Sasada et al., Cancer, 2003, 98(5):1089-1099), breast (Liyanage et al., J. Immunol., 2002, 169(5):2756-2761), lung (Woo et al., Cancer Res., 2001, 61(12):4766-72), and pancreas (Liyanage et al., J Immunol., 2002, 169(5):2756-2761). The regulatory T cells are recruited to the tumor site in response to chemokines secreted by the tumor cells. See e.g., Curiel et al., Nat. Med., 2004, 10:942-949. An increase in the number of regulatory T cells may also correlate with poor prognosis (Curiel et al., Nat. Med., 2004, 10:942-949; Sasada et al., Cancer, 2003, 98:1089-1099). Conversely, regulatory T cells are observed to decrease following chemotherapy (Beyer et al., Blood, 2005, 106:2018-2025). Such non-malignant cells can also be fibroblasts, myofibroblasts, glial cells, epithelial cells, adipocytes, vascular cells (including blood and lymphatic vascular endothelial cells and pericytes), resident and/or recruited inflammatory and immune (e.g., macrophages, dendritic cells, myeloid suppressor cells, granulocytes, lymphocytes, etc.), resident and/or recruited cells that are capable of giving rise to or differentiating into any of the above-noted non-malignant cells, and any functionally distinct subtypes of the above-noted cells as known in the art.

In alternative embodiments, a fusion protein including an anti-apoptotic Bcl-2 family member is useful for reducing apoptosis or promoting proliferation. Accordingly, compositions including such fusion proteins may, if desired, be combined with any standard therapy typically used to treat a disease or disorder characterized by excess cell death. In one embodiment, the standard therapy is useful for the treatment of cell death or apoptosis associated with hypoxia, receipt of a cell, tissue or organ transplantation, receipt of chemotherapy, or receipt of radiation therapy. Such methods are known to the skilled artisan and described in Remington's Pharmaceutical Sciences by E. W. Martin.

Alternatively, a fusion protein including an anti-apoptotic Bcl-2 family member can be administered in combination with a chemotherapeutic, such that the fusion protein reduces the toxic effects typically associated with chemotherapy. For example, a patient that receives a chemotherapeutic and a fusion protein is less likely to suffer from side-effects associated with the apoptosis of normal cells (e.g., reduced neutrophil count) than a patient that receives only the chemotherapeutic. A composition of the invention is administered prior to, concurrent with, or following the administration of any one or more of the following: a chemotherapeutic agent, radiation agent, hormonal agent, biological agent, an anti-inflammatory agent. Exemplary chemotherapeutic agents include tamoxifen, trastuzamab, raloxifene, doxorubicin, fluorouracil/5-fu, pamidronate disodium, anastrozole, exemestane, cyclophos-phamide, epirubicin, letrozole, torcmifene, fulvestrant, fluoxymesterone, trastuzumab, methotrexate, megastrol acetate, docetaxel, paclitaxel, testolactone, axiridine, vinblastine, capecitabine, goselerin acetate, zoledronic acid, taxol, vinblastine, and vincristine.

If necessary to reduce a systemic immune response to the fusion proteins, immunosuppressive therapies can be administered in combination with the fusion proteins including an anti-apoptotic Bcl-2 family member. Examples of immunosuppressive therapies include, but are not limited to, systemic or topical corticosteroids (Suga et al., Ann. Thorac. Surg., 73:1092-7, 2002), cyclosporin A (Fang et al., Hum. Gene Ther., 6:1039-44, 1995), cyclophosphamide (Smith et al., Gene Ther., 3:496-502, 1996), deoxyspergualin (Kaplan et al., Hum. Gene Ther., 8:1095-1104, 1997) and antibodies to T and/or B cells such as anti-CD40 ligand, anti CD4 antibodies, or anti-CD20 antibody (Rituximab) (Manning et al., Hum. Gene Ther., 9:477-85, 1998). Such agents can be administered before, during, or subsequent to administration of the fusion proteins. Such agents can be administered from about 10 mg/week to about 1000 mg/week, from about 40 mg/week to about 700 mg/week, or from about 200 mg/week to about 500 mg/week for 2, 3, 4, 5, 6, or 7 weeks. Courses of treatment can be repeated as necessary if the subject remains responsive (e.g., the symptoms of cancer are static or decreasing).

A "subject" can be a mammal in need of treatment, such as a human or veterinary patient (e.g., rodent, such as a mouse or rat, a cat, dog, cow, horse, sheep, goat, or other livestock). In some embodiments, a "subject" may be a clinical patient, a clinical trial volunteer, an experimental animal, etc. The subject may be suspected of having or at risk for having a condition characterized by cell proliferation, be diagnosed with a condition characterized by cell proliferation, or be a control subject that is confirmed to not have a condition characterized by cell proliferation, as described herein. Diagnostic methods for conditions characterized by cell proliferation and the clinical delineation of such diagnoses are known to those of ordinary skill in the art. The subject may be suspected of having or at risk for having a condition characterized by cell death, be diagnosed with a condition characterized by cell death, or be a control subject that is confirmed to not have a condition characterized by cell death, as described herein. Diagnostic methods for conditions characterized by cell death and the clinical delineation of such diagnoses are known to those of ordinary skill in the art.

The composition can be a liquid solution, suspension, emulsion, sustained release formulation, or powder, and can be formulated with a pharmaceutically acceptable carrier. The composition can be formulated as a suppository, with traditional binders and carriers such as triglycerides. The term "pharmaceutically-acceptable carrier" refers to a carrier medium or vehicle which does not interfere with the effectiveness of the biological activity of the active ingredients and which is not toxic to the host or subject.

Fusion proteins can be delivered along with a pharmaceutically-acceptable vehicle. In one example, the vehicle may enhance the stability and/or delivery properties. Thus, the disclosure also provides for formulation of the fusion protein with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the fusion proteins. Alternatively, or in addition, the fusion protein formulations can include additives to stabilize the protein in vivo, such as human serum albumin, or other stabilizers for protein therapeutics known in the art. Fusion protein formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions containing one or more fusion proteins can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In some embodiments, the fusion protein is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7(8):2407-14, 2006).

In some embodiments, a fusion protein including an anti-apoptotic Bcl-2 family member polypeptide (such as a cpIL2-Bcl-xL fusion protein) can be used for inhibiting the apoptosis or promoting the proliferation of immune cells during the production of a therapeutic or prophylactic vaccine. In some embodiments, the fusion protein including an anti-apoptotic Bcl-2 family member polypeptide (such as a cpIL2-Bcl-xL fusion protein) is used in combination with a GM-CSF Bcl-xL fusion protein or with GM-CSF alone. In general, the vaccine includes a cell (e.g., an immune cell) derived from a subject that requires vaccination. In general, the cell is obtained from a biological sample of the subject, such as a blood sample or a bone marrow sample. Preferably, an immune cell is obtained from the subject, and the cell is cultured in vitro to obtain a population of immune cells. The cultured cells are contacted with an antigen (e.g., a cancer antigen) in the presence of a fusion protein of the invention. Desirably, an immune cell contacted with the antigen in the presence of the fusion protein is at reduced risk of apoptosis relative to an immune cell contacted in the absence of the fusion protein. Optionally, the contacted cells are expanded in number in vitro. The cells are then re-introduced into the subject where they enhance or elicit an immune response against an antigen of interest (e.g., a cancer antigen). Methods for producing such vaccines are known in the art and are described, for example, by Zhu et al., J Neurooncol. 2005 August; 74(1):9-17; Nair et al., Int. J. Cancer 1997; 70:706-715; and Fong et al., Annu. Rev. Immunol. 2000; 18:245-273.

Typically vaccines are prepared in an injectable form, either as a liquid solution or as a suspension. Solid forms suitable for injection may also be prepared as emulsions, or with the polypeptides encapsulated in liposomes. The cells are injected in any suitable carrier known in the art. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Vaccines are administered in a manner compatible with the dose formulation. By an effective amount is meant a single dose, or a vaccine administered in a multiple dose schedule, that is effective for the treatment or prevention of a disease or disorder. Preferably, the dose is effective to inhibit the growth of a neoplasm. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner.

In some embodiments, a fusion protein including an anti-apoptotic Bcl-2 or pro-apoptotic Bcl-2 family member polypeptide, as desired, can be used in ex vivo methods. For example, cells (e.g., peripheral blood lymphocytes or purified populations of lymhocytes isolated from a patient and placed or maintained in culture) can be cultured in vitro in culture medium and the contacting step can be affected by adding the IL-2 fusion protein to the culture medium. The culture step can include further steps in which the cells are stimulated or treated with other agents, e.g., to stimulate or reduce proliferation, or to expand or deplete a population of cells (e.g., regulatory T cells). In some embodiments, fusion proteins according to the invention can be used to propagate and expand engineered T cells for, for example, adoptive cell transfer therapy and chimeric antigen receptor (CAR) therapy (CAR-T). The cells are then administered to the patient.

The pharmaceutical compositions described herein include one or more fusion proteins in an amount effective to achieve the intended purpose. Typically, compositions including a fusion protein containing an anti-apoptotic Bcl-2 family member are administered to a patient already suffering from a disease, disorder or condition characterized by cell death, or at risk for such a disease, disorder or condition, in an amount sufficient to cure or at least partially arrest a symptom associated with cell death or enhance cell growth. In alternative embodiments, compositions including a fusion protein containing an pro-apoptotic Bcl-2 family member are administered to a patient already suffering from a disease, disorder or condition characterized by cell proliferation, or at risk for such a disease, disorder or condition, in an amount sufficient to cure or at least partially arrest a symptom associated with cell proliferation or reduce cell growth.

The skilled person will therefore recognize that the dosage to be administered is not subject to defined limits. Prior to administration for therapeutic purposes, the dosage of the fusion protein may need to be modified or adapted for the particular purpose, for example the concentration of fusion protein needed for whole body administration may differ from that used for local administration. Similarly, the toxicity of the therapeutic may change depending upon the mode of administration and overall composition being used (e.g., buffer, diluent, additional chemotherapeutic, etc.).

An "effective amount" of a pharmaceutical composition according to the invention includes a therapeutically effective amount or a prophylactically effective amount. A "therapeutically effective amount" refers to an amount of the fusion protein effective, at dosages and for periods of time necessary, that ameliorates the symptoms of the disease, disorder or condition to be treated. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the fusion protein are outweighed by the therapeutically beneficial effects. Determination of a therapeutically effective dose of a compound is well within the capability of those skilled in the art. For example, the therapeutically effective dose can be estimated initially either in cell culture assays, or in animal models, such as those described herein. A "prophylactically effective amount" refers to an amount of the fusion protein effective, at dosages and for periods of time necessary, that achieves the desired prophylactic result, such as delay in onset of symptoms of an autoimmune disorder or continued remission of a cancer. Animal models can also be used to determine the appropriate concentration range and route of administration. Such information can then be used to determine useful doses and routes for administration in other animals, including humans, using standard methods known in those of ordinary skill in the art.

Concentration of the fusion protein in the final formulation can be at least 0.1 mg/mL, such as at least 1 ng/mL or at least 1 ug/mL or at least 1 mg/mL. For example, the concentration in the final formulation can be between about 0.01 ug/mL and about 1,000 ug/mL. In one example, the concentration in the final formulation is between about 0.01 mg/mL and about 100 mg/mL.

In some embodiments, a fusion protein including an anti-apoptotic Bcl-2 family protein, or fragment thereof, is administered at concentrations ranging from about 10 ng/mL to about 10,000 ng/mL, or any value therebetween, such as about 25 ng/mL, 50 ng/mL, 75 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1000 ng/mL, 1500 ng/mL, 2000 ng/mL, 2500 ng/mL, 3000 ng/mL, 3500 ng/mL, 4000 ng/mL, 4500 ng/mL, 5000 ng/mL, 5500 ng/mL, 6000 ng/mL, 6500 ng/mL, 7000 ng/mL, 7500 ng/mL, 8000 ng/mL, 8500 ng/mL, 9000 ng/mL, 9500 ng/mL, or 10000 ng/mL.

In some embodiments, a fusion protein including an pro-apoptotic Bcl-2 family protein, or fragment thereof, is administered at concentrations ranging from about 0.1 ng/mL to about 10,000 ng/mL.

However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances dosage levels below the lower limit of the aforesaid range may be more than adequate, while in other cases still larger doses may be employed without causing harmful side effects, for example, by first dividing the larger dose into several smaller doses for administration throughout the day.

One of ordinary skill in the art will appreciate that the dosage will depend, among other things, upon the type of fusion protein being used and the type of disorder or condition being treated.

In general, the fusion proteins according to the present disclosure contain substantially human sequences and are therefore less antigenic than, for example, immunotoxins or other molecules that contain non-human sequences. In some embodiments, the fusion proteins according to the present disclosure contain at least 80%, for example, 80%, 85%, 90%, 95%, 96%, 97%, 98%, 99% or 100% human sequences. In some embodiments, the fusion proteins according to the present disclosure can be administered at substantially lower doses than for example, immunotoxins, or native IL-2.

In some embodiments, the fusion proteins may elicit some level of antibody response when administered to a subject, which in some cases may lead to undesirable side effects. Therefore, if necessary, the antigenicity of the fusion proteins can be assessed as known in the art and/or described herein. For example, in vivo toxic effects of the fusion proteins can be evaluated by measuring their effect on animal body weight during treatment and by performing hematological profiles and liver enzyme analysis after the animal has been killed. The general toxicity of the fusion proteins can be tested according to methods known in the art. For example, the overall systemic toxicity of the fusion proteins can be tested by determining the dose that kills 100% of mice (i.e. $LD_{100}$) or kills 50% of mice (i.e. $LD_{50}$) following a single intravenous injection. Doses that are at least about 2, 5, or 10-fold less than the $LD_{100}$ or $LD_{50}$ can be selected for administration into other mammals, such as a human.

The kinetics and magnitude of the antibody response to the fusion proteins described herein can be determined, for example, in immunocompetent mice and can be used to facilitate the development of a dosing regimen that can be used in an immunocompetent human. Immunocompetent mice such as the strain C57-BL6 are administered intravenous doses of fusion protein. The mice are killed at varying intervals (e.g. following single dose, following multiple doses) and serum obtained. An ELISA-based assay can be used to detect the presence of anti-fusion protein antibodies.

Serum samples from mice can be assessed for the presence of anti-fusion protein antibodies as known in the art. As another example, epitope mapping can also be used to determine antigenicity of proteins as described in Stickler, et al., J. Immunotherapy, 23:654-660, 2000. Briefly, immune cells known as dendritic cells and CD4+ T cells are isolated from the blood of community donors who have not been exposed to the protein of interest. Small synthetic peptides spanning the length of the protein are then added to the cells in culture. Proliferation in response to the presence of a particular peptide suggests that a T cell epitope is encompassed in the sequence. This peptide sequence can subsequently be deleted or modified in the fusion protein thereby reducing its antigenicity.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

Administration of the fusion proteins can be intralesionally, for instance by direct injection directly into the apoptotic tissue site, into a site that requires cell growth, into a site where a cell, tissue or organ is at risk of cell death, or into a site of hyperproliferation or into a tumor. Alternatively, the fusion protein can be administered systemically. For methods of combination therapy comprising administration of a fusion protein in combination with a chemotherapeutic agent, the order in which the compositions are administered is interchangeable. Concomitant administration is also envisioned Typically in the treatment of cancer, fusion proteins are administered systemically to patients, for example, by bolus injection or continuous infusion into a patient's bloodstream. Alternatively, the fusion proteins may be administered locally, at the site of a tumor (intratumorally). When a fusion protein is administered intratumorally, the administration can be via any route, e.g., locally, regionally, focally, systemic, convection enhanced delivery or combinations thereof.

When used in conjunction with one or more known chemotherapeutic agents, the compounds can be administered prior to, or after, administration of the chemotherapeutic agents, or they can be administered concomitantly. The one or more chemotherapeutics may be administered systemically, for example, by bolus injection or continuous infusion or they may be administered orally.

For administration to an animal, the pharmaceutical compositions can be formulated for administration by a variety of routes. For example, the compositions can be formulated for topical, rectal or parenteral administration or for administration by inhalation or spray. The term parenteral as used herein includes subcutaneous injections, intravenous, intramuscular, intrathecal, intrasternal injection or infusion techniques. Direct injection or infusion into a tumor is also contemplated. Convection enhanced delivery can also be used to administer the fusion protein.

In one example, the fusion protein can be injected into a subject having cancer, using an administration approach similar to the multiple injection approach of brachytherapy. For example, multiple aliquots of the purified fusion protein in the form of a pharmaceutical composition or formulation and in the appropriate dosage units, may be injected using a needle. Alternative methods of administration of the fusion proteins will be evident to one of ordinary skill in the art. Such methods include, for example, the use of catheters, or implantable pumps to provide continuous infusion of the fusion protein to the subject in need of therapy.

As is known in the art, software planning programs can be used in combination with brachytherapy treatment and ultrasound, for example, for placement of catheters for infusing fusion proteins to treat, for example, brain tumors or other localized tumors. For example, the positioning and placement of the needle can generally be achieved under ultrasound guidance. The total volume, and therefore the number of injections and deposits administered to a patient, can be adjusted, for example, according to the volume or area of the organ to be treated. An example of a suitable software planning program is the brachytherapy treatment planning program Variseed 7.1 (Varian Medical Systems, Palo Alto, Calif.). Such approaches have been successfully implemented in the treatment of prostate cancer among others.

The in vivo or in vitro expression of a fusion protein including an anti-apoptotis Bcl-2 family member (e.g., a IL-2-Bcl-XL fusion protein), or fragment thereof is another therapeutic approach for promoting the survival or proliferation of a cell at risk of undergoing cell death. Nucleic acid molecules encoding such fusion proteins can be delivered to cells of a subject that are at risk for apoptosis. The expression of a fusion protein in a cell promotes proliferation, prevents apoptosis, or reduces the risk of apoptosis in that cell or in a target cell or tissue. The nucleic acid molecules must be delivered to the cells of a subject in a form in which they can be taken up so that therapeutically effective levels of the fusion protein can be produced. In some embodiments, the fusion protein is administered to a subject prior to the subject starting a therapy, such as an immunotherapy. Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a fusion protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med. 323:370, 1990; Anderson et al., U.S. Pat. No. 5,399,346). Most preferably, a viral vector is used to administer a chimeric polynucleotide to a target cell, tissue, or systemically.

Non-viral approaches can also be employed for the introduction of a therapeutic to a cell requiring modulation of cell death (e.g., a cell of a patient). For example, a nucleic acid molecule can be introduced into a cell by administering the nucleic acid molecule in the presence of lipofection (Feigner et al., Proc. Natl. Acad. Sci. U.S.A. 84:7413, 1987; Ono et al,. Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of a fusion protein into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The present invention will be further illustrated in the following examples.

EXAMPLES

Example 1 proS2-BAD was prepared using standard techniques.

More specifically, cDNA of proS2-BAD was PCR cloned into BamHI/XhoI sites of a pGW07 E. coli, expression vector (FIG. 1). The obtained vector was verified by DNA sequencing (FIGS. 2A and B).

Protein expression was performed in E. coli cells. proS2-BAD protein was expressed in IL cultures in insoluble form, purified under denaturing conditions using IMAC, followed by "quick dilution" protein refolding. Refolding by "quick dilution" generated intact proteins free of aggregates, as determined by non-reducing SDS-PAGE. Final sample size and concentrations were as follows: proS2-BAD (pH 7.8) was about 1 mL at 0.16 mg/mL, determined by UV280 nm (UV280 nm Abs at1 mg/ml=1.25); and proS2-BAD (pH 6.0) was about 1 mL at 0.09 mg/mL, determined by UV280 nm (UV280 nm Abs at 1 mg/mL=1.17). Protein was stored in a storage buffer composition 500 nM NaCL, 10 mM Na-Phosphate, pH 6.0 or 7.8, 1% glycerol, 1 µM EDTA, 0.01% Tween 20.

BL21(DE3)pLysS-RARE2 cells were transformed with proS2-BAD protein expression constructs, plated on LB plates supplemented with Amp at 100 µg/mL, and incubated overnight at 37° C. The next day, colonies from the plate were scraped and re-suspended in liquid LB medium with 100 µg/mL of Amp. The cultures were then grown at 37° C., with aeration, and protein expression was induced by 1 mM IPTG when the cell culture reached an $OD_{600}$ of about 0.5. Induction lasted for about 4 hours at 30° C. The cell pellet was then collected and stored at −20° C. 10 µL samples of uninduced and induced culture were lysed by boiling at 95° C. For 10 minutes in 50 µL of reducing protein loading buffer and run on an SDS-PAGE gel. Cells from a 1 mL sample collected at 4 hours post-induction were lysed in hypotonic buffer, sonicated and centrifuged for 10 minutes at 13,000 rpm. Aliquots from the soluble and insoluble fraction were boiled in reducing protein loading buffer and analysed on an SDS-PAGE gel. Estimated expression levels observed for proS2-BAD protein was more about 20 mg/L of crude material proS2-BAD were mainly in the insoluble fraction.

The cell pellets from the induced cultures were lysed at room temperature and the inclusion bodies fraction was collected and washed with PBS-T. The insoluble material was solubilized in 8M Urea and bound to 3 mL Ni-charged resin. The resin was washed with 15 CV of wash buffer and the bound protein was eluted in 8 CV elutions of step gradient of imidazole in wash buffer 7.5 µL from each fraction was analyzed on a SDS-PAGE gel. The fractions with the highest amount of proS2-BAD were combined and refolded. The remaining fractions were stored at −20° C.

4 ml of 500-1 mM imidazole fractions containing proS2-BAD was quickly diluted into 200 mL of refolding buffer (500 mM NaCl, 10 mM Na-Phosphate, pH 6.0 or 7.8, 1% Glycerol, 10 µM EDTA, 0.01% Tween), incubated overnight at room temperature, spun down for 20 minutes at 4,000 rpm at 4° C., concentrated to 3 mL using an Amicon 10 kDa MWCO, and buffer exchanged into storage buffer (500 mM NaCl, 10 mM Na-Phosphate, pH 6.0 or 7.8, 1% Glycerol, 1 µM EDTA, 0.01% Tween) using a DG-10 column. Final sample concentrations were as follows: 1 mL of proS2-BAD (pH 7.8) at about 0.16 mg/mL, and 1 mL of proS2-BAD (pH 6.0) at about 0.09 mg/mL. The final samples were run on an SDS-PAGE gel.

The final concentration of cpS4-BAD was about 3.5 mL at about 0.23 mg/mL. The final sample was run on an SDS-PAGE gel.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of enhancing cell survival or proliferation, or inhibiting cell death or apoptosis of a target cell expressing an interleukin-2 receptor (IL-2R), the method comprising contacting the target cell with a fusion protein, a nucleic acid molecule encoding the fusion protein or a vector comprising the nucleic acid molecule, wherein the fusion protein comprises an interleukin-2 (IL-2) and a Bcl-2 family polypeptide, wherein the IL-2 comprises an amino acid sequence selected from the group consisting of SEQ ID NO:2, SEQ ID NO:3, and SEQ ID NO:4, and wherein the Bcl-2 family polypeptide is an anti-apoptotic Bcl-2 family polypeptide Bcl-xL comprising the amino acid sequence of SEQ ID NO:7.

2. The method of claim 1, wherein the target cell is a T cell or a natural killer cell.

3. The method of claim 2, wherein the target cell is an engineered cell.

4. The method of claim 1, wherein the fusion protein comprises the amino acid sequence of SEQ ID NO:11.

5. The method of claim 1, wherein the fusion protein comprises the amino acid sequence of SEQ ID NO:12.

6. The method of claim 1, wherein the IL-2 is circularly permuted (cp).

7. The method of claim 1, wherein the IL-2 is a mutant IL-2 selective for binding to a chain of an IL-2 receptor (IL-2R).

8. The method of claim 7, wherein the mutant IL-2 has increased selectivity for IL-2Rβ relative to native IL-2.

9. The method of claim 8, wherein the fusion protein further comprises a linker.

10. The method of claim 9, wherein the linker has the sequence Gly-Ser (GS) or the linker includes the amino acid sequence Gly-Ser (GS).

11. The method of claim 9, wherein the linker is bifunctional or polyfunctional.

12. The method of claim 9, wherein the linker is a peptide linker.

13. The method of claim 12, wherein the peptide linker is a protease cleavable peptide linker.

14. The method of claim 1, wherein the nucleic acid molecule comprises the nucleic acid sequence of SEQ ID NO:10.

15. The method of claim 1, wherein the IL-2 is encoded by a nucleic acid sequence comprised in the nucleic acid molecule selected from the group consisting of SEQ ID NO:5 and SEQ ID NO:6.

16. The method of claim 15, wherein the IL-2 is encoded by a nucleic acid sequence comprised in the nucleic acid molecule of SEQ ID NO:5.

17. The method of claim 15, wherein the IL-2 is encoded by a nucleic acid sequence comprised in the nucleic acid molecule of SEQ ID NO:6.

* * * * *